United States Patent [19]
Wong et al.

[11] Patent Number: 6,111,084
[45] Date of Patent: Aug. 29, 2000

[54] FUOPEPTIDE MIMETICS

[75] Inventors: Chi-Huey Wong, Rancho Santa Fe, Calif.; Thomas F. J. Lampe, Wuppertal, Germany

[73] Assignee: The Scripps Research Institute, La Jolla, Calif.

[21] Appl. No.: 09/088,411

[22] Filed: Jun. 1, 1998

Related U.S. Application Data

[63] Continuation-in-part of application No. 08/933,775, Sep. 19, 1997, Pat. No. 5,962,660, which is a continuation-in-part of application No. PCT/EP96/01244, Mar. 21, 1996, which is a continuation-in-part of application No. 08/519,203, Aug. 25, 1995, Pat. No. 5,614,615, which is a continuation-in-part of application No. 08/407,912, Mar. 21, 1995, Pat. No. 5,599,915.

[51] Int. Cl.⁷ ................................................... C07H 15/04
[52] U.S. Cl. ..................... 536/17.2; 536/29.1; 530/322; 562/533; 562/570
[58] Field of Search .................................. 536/17.2, 29.1; 530/322; 562/553, 570; 514/19

[56] References Cited

PUBLICATIONS

Wu, Angew. Chem. Int. Ed. Engl 35, 88, 1996.
Lin, J. Am. Chem. Soc. 118, 6826, 1996.

*Primary Examiner*—David Luxton
*Attorney, Agent, or Firm*—Donald G. Lewis

[57] ABSTRACT

Bioactive fucopeptides and libraries of fucopeptides having advanced activities against P-selectin as sialyl Lewis X mimetics with $IC_{50}$ values in the low mM range are synthesized by solid phase synthesis using para-acyloxymethylenzlidene acetal (p-AMBA) as an anchoring group. A rapid parallel synthesis is employed which proceeds with a bi-directional functionalization of glycosylated amino acid derivatives.

3 Claims, 10 Drawing Sheets

100

200

300

400

500

600

700

| #[a] | yield for 9[b] | yield for 10[c] | XR¹ | R³ | E-selectin IC$_{50}$ [mM] | P-selectin IC$_{50}$ [mM] |
|---|---|---|---|---|---|---|
| -a | 62% | 88% | OEt |  | 0.8 | 3.0 |
| -b | 65% | 97% | OEt |  | 4.0 | 0.66 |
| -c | 47% | 76% |  |  | 3.2 | 0.057 |
| -d | 58% | 67% |  |  | 4.1 | 0.030 |
| -e | 49% | 81% |  |  | 1.8 | 0.059 |
| -f | 51% | 95% |  |  | 3.2 | 0.256 |
| -g | 65% | 94% | OEt |  | 0.7 | >1.0 |
| -h | 55% | 90% |  |  | 4.1 | 0.017 |

FUOPEPTIDE MIMETICS

GOVERNMENT RIGHTS

This invention was made with government support under Grant No. CHE 9310081 awarded by the National Science Foundation. The U.S. government has certain rights in the invention.

CROSS-REFERENCE TO RELATED APPLICATION

The present application is a continuation-in-part of U.S. copending patent application Ser. No. 08/933,775, filed Sep. 19, 1997, now U.S. Pat. No. 5,962,660 which is a continuation-in-part of P.C.T patent application No. PCT/EP 96/01244, filed Mar. 21, 1996, which is a continuation-in-part of U.S. patent application Ser. No. 08/519,203, filed Aug. 25, 1995, issued on Mar. 25, 1997 as U.S. Pat. No. 5,614,615, which is a continuation-in-part of U.S. patent application Ser. No. 08/407,912, filed Mar. 21, 1995, issued on Feb. 4, 1997 as U.S. Pat. No. 5,599,915, whose disclosures are incorporated herein by reference.

TECHNICAL FIELD

The present invention relates to Sialyl Lewis X mimetics and methods for synthesizing for such compounds. More particularly, the present invention comprises a novel anchoring group (para-Acyloxymethylbenzylidene acetal, p-AMBA) which enables the bi-directional functionalization of glycosylated amino acid derivatives and thus the rapid parallel synthesis of fucopeptides as Sialyl Lewis X mimetics on solid phase, leading to the discovery of new mimetics against P-selectin with $IC_{50}$ values in the low mM range.

BACKGROUND

During an inflammatory response, injured tissues release cytokines that trigger the expression of P-selectin followed by E-selectin on the endothelium. The selectins then interact with Sialyl Lewis X (sLex), a tetrasaccharide of the terminal unit of surface glycoproteins and glycolipids. This interaction between the selecting and sLex leads to leukocyte "rolling", followed by protein-protein interactions (integrins CD 11/18, ICAM-1 ligand) causing firmer adhesion and eventually extravasation of leukocytes into the endothelium. Blocking the sLex/selectin interactions at an early stage of the inflammatory cascade, especially the P-selectin-ligand interactions, is an effective way of treating acute and perhaps chronic inflammatory diseases (Buerke et al., *J. Clin. Invest.* 1994, 1140; Giannis et al., *Angew. Chem.* 1994, 106, 188).

Though sLex is being clinically evaluated as a drug candidate for the treatment of reperfusion injury, it can only be administered by injection with a high dose, as it binds the selectins weakly and is orally inactive and unstable in the blood. sLex has, however, served as a useful lead for the design of simpler and better low molecular weight compounds as selectin antagonists. On the basis of the crystal structure of E-selectin, NMR studies of the conformations of sLex in solution and bound to E-, P- and L-selectin (Ichikawa et al. *J. Am. Chem. Soc.* 1992, 114, 9283; Cooke et al. *Biochemistry* 1994, 33, 10591; Scheffler et al. *Angew. Chem.* 1995, 107, 2034; *Angew. Chem. Int. Ed. Engl.* 1995, 34, 1841; Poppe et al., *J. Am. Chem. Soc.* 1997, 119, 1727), and the structure activity studies of sLex derivatives and mimetics (Bradley et al. *Glycobiology,* 1993, 3, 633; Stahl et al. *Angew. Chem.,* 1994, 106, 2186, *Angew. Chem. Int. Ed. Engl.,* 1994, 33, 7096; DeFrees et al., *J. Am. Chem. Soc.,* 1993, 115, 7549), the crucial functional groups in space required for the sLex epitope binding to the selectins have been elucidated. Using this recognition model, a vast number of structurally diverse low molecular weight compounds as sLex mimetics have been prepared. Some of them exhibit equal or higher affinity towards the selectins than sLex (Wu et al. *Angew. Chem.* 1996, 108, 106; *Angew. Chem. Int. Ed. Engl.* 1996, 35, 88; Lin et al., *J. Am. Chem. Soc.* 1996, 118, 6826; Wong et al. ibid., 1997, 119, 8152; Kolb et al., *Chem. Eur. J.,* 1997, 3, 1571) as shown in FIG. 1.

Recently, interest in solid phase synthesis has increased dramatically, mainly due to the excitement emerging from the concept of combinatorial chemistry as a powerful tool for the discovery of biologically active compounds and for lead optimization (Gallop et al. *J. Med. Chem.* 1994, 37, 1233; Gordon et al., ibid. 1994, 37, 1385; Fruchtel et al., *Angew. Chem.* 1996, 108, 19; *Angew. Chem. Int. Ed. Engl.* 1996, 35, 17; Balkenhohl et al., ibid. 1996, 108, 2436; ibid. 1996, 35, 2288; *Combinatorial Peptide and Nonpeptide Libraries,* Ed. G. Jung, VCH, Weinheim, 1996; Lam et al., *Chem. Rev.,* 1997, 97, 411; Nefzi et al.; Ostresh et al., ibid. 1997, 97, 449). In particular, the multiple or parallel synthesis of individual compounds on solid phase is considered to be a promising approach to rapid optimization of previously identified lead structures.

What is needed are new strategies applicable to the parallel and/or combinatorial synthesis of a designed library of O- and C-C-fucopeptides structurally related to 2, and analogs nearly as active or more active as SLex against E-selectin.

SUMMARY OF THE INVENTION

The invention is directed to Sialyl Lewis X mimetics and methods of synthesis for such compounds. More particularly, the invention is directed to a novel anchoring group (para-Acyloxymethylbenzylidene acetal, p-AMBA) which enables the bi-directional functionalization of glycosylated amino acid derivatives and thus the rapid parallel synthesis of fucopeptides as Sialyl Lewis X mimetics on solid phase. The methodolgy provides an efficient means for the discovery of new mimetics against P-selectin with $IC_{50}$ values in the low mM range.

One aspect of the invention is directed to sialyl Lewis mimetics represented by the following structure:

In the above structure, X is a radical selected from a group consisting —O— and —NH—; $R_4$ is a radical selected from a group consisting of —(CH$_2$CH$_2$—O—), —(CH$_2$)$_m$—CH$_3$, —(C$_1$–C$_{20}$ alkyl), -phenyl, -benzyl, -nitrobenzyl, -trityl, -allyl, -furoyl, -cinnamoyl, -thiophenesulfonyl, —CH$_2$CO$_2$—(C$_l$–C$_{20}$ alkyl) —CH$_2$CO$_2$-allyl, and —CH$_2$CO$_2$H; $1 \leq n \leq 10$; $1 \leq m \leq 10$; $R_{10}$ is a radical represented by the formula: —CH(OH)—CH$_2$(OH); —CH(OBn)—CH$_2$(OH), —CH(OH)—CH$_2$(OBn); $R_{11}$ is a radical selected from a group consisting of —(CH$_2$)$_p$CO$_2$H, (CH$_2$)$_p$CO$_2$Bn, —(CH$_2$)$_p$PO(OBn)$_2$ and —(CH$_2$)$_p$PO(OH)$_2$; $1 \leq p \leq 5$.

Another aspect of the invention is directed to libraries of the above sialyl Lewis mimetics.

Another aspect of the invention is directed to an anchor group for anchoring a carbohydrate to a support. The anchor group is represented by the following structure:

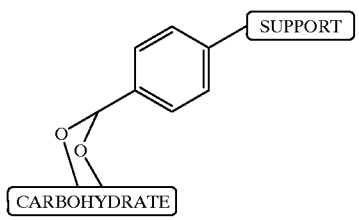

The anchor group is linked to the carbohydrate by an acetal as represented above. A preferred anchor group is represented by the following structure:

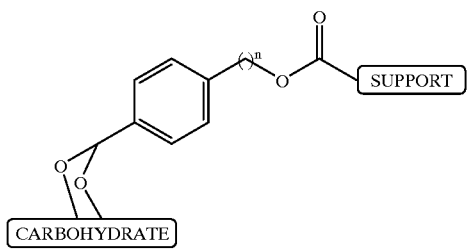

The preferred anchor group is anchored to the support by an ester bond as represented above, where $1 \leq n \leq 5$. A preferred carbohydrate is a Sialyl Lewis fucopeptide mimetic.

Another aspect of the invention is directed to a method for synthesizing a sialyl Lewis mimetic. The method employs a parallel synthesis strategy. In the first step, a first intermediate is attached to an anchor molecule. The first intermediate is represented by the following structure:

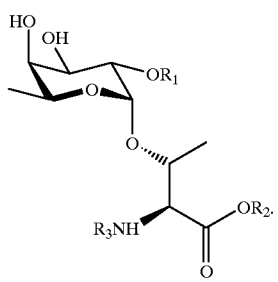

In the above structure, $R_1$ is an alcohol blocking group; $R_2$ is a carboxy acid blocking group; and $R_3$ is an amine blocking group. The anchor molecule is represented by the following structure:

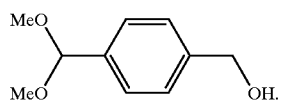

Attachment of the first intermediate to the anchor molecule is achieved by for forming a benzylidene acetal having a free hydroxyl moiety represented by the following structure:

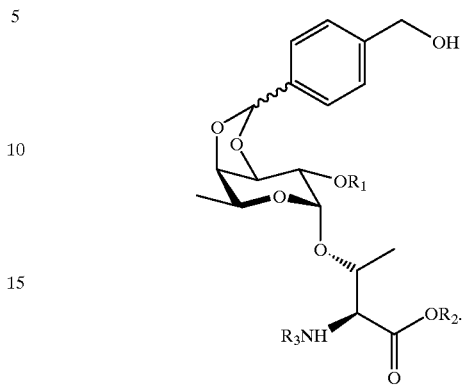

The free hydroxyl moiety of the benzylidene acetal is then anchored to a support molecule, the support molecule being of a type which includes a terminal carboxylic acid group. Anchorage of the free hydroxyl moiety of the benzylidene acetal to a support molecule results in the formation of an immobilized fucoside represented by the following structure:

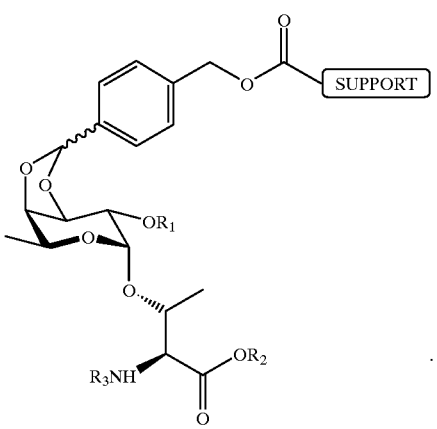

The carboxy acid blocking group ($R_2$) of the immobilized fucoside is then removed for deblocking the carboxy acid and forming an immobilized fucoside having a free C-terminal carboxy acid group.

The C-terminal carboxy acid group is then reacted with a nucleophile to form a first C-terminal functionalized immobilized fucoside. The nucleophile is represented by the formula $R_4$-XH, wherein X is a radical selected from a group consisting —O— and —NH—; and $R_4$ is a radical selected from a group consisting of —(CH$_2$CH$_2$—O—)$_n$—(CH$_2$)$_m$—CH$_3$, —(C$_1$–C$_{20}$ alkyl), -phenyl, -benzyl, -nitrobenzyl, -trityl, -allyl, -furoyl, -cinnamoyl, -thiophenesulfonyl, —CH$_n$CO$_2$—(C$_1$–C$_{20}$ alkyl) —CH$_2$CO$_2$-allyl and —CH$_n$CO$_2$H; $1 \leq n \leq 10$; $1 \leq m \leq 10$. The first C-terminal functionalized immobilized fucoside is represented by the formula:

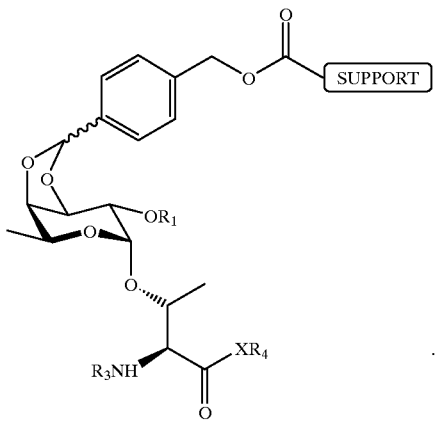

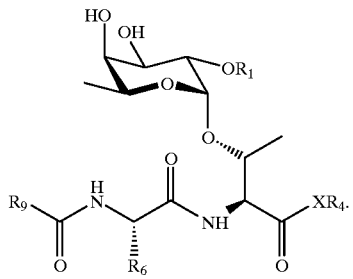

The $R_1$ group, the $R_6$ group and the $R_9$ group of the advanced intermediate are then deprotected for forming sialyl Lewis mimetics represented by the following structure:

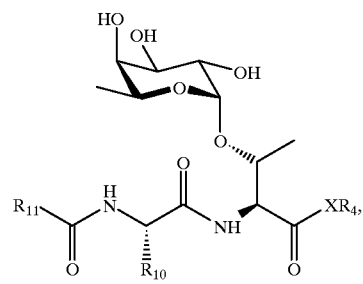

where $R_{10}$ is a radical represented by the formula —CH(OH)—CH$_2$(OH); and $R_{11}$ is a radical selected from a group consisting of —(CH$_2$)$_p$CO$_2$H, and —(CH$_2$)$_p$PO(OH)$_2$.

Another aspect of the invention is directed to a method for anchoring a carbohydrate to a support. The method employs the step of linking the carbohydrate to the support with an anchor group for forming a product represented by the following structure:

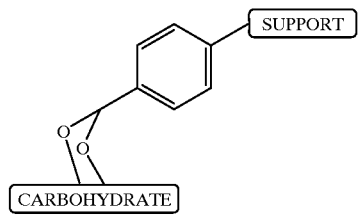

The anchor group is linked to the carbohydrate by an acetal, as represented in the above structure.

Another aspect of the invention is directed to a method for decoupling a carbohydrate from a constuct represented by the following structure:

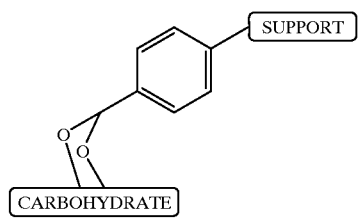

The amino blocking group ($R_3$) of the first C-terminal functionalized immobilized fucoside is then removed for deblocking the amino group and forming a second C-terminal functionalized immobilized fucoside having a free N-terminal amino group.

The free N-terminal amino group is then reacted with an acceptor represented by the formula $R_{12}NH(CHR_6)_nCOY$ for forming a first C/N-terminal functionalized immobilized fucoside. $R_6$ of the acceptor is a radical selected from a group consisting of —CH(OR$_7$)—CH$_2$(OR$_8$), where $R_7$ and $R_8$ are independently selected from a group consisting of hydrogen, phenyl and benzyl. Y of the acceptor is a radical selected from a group consisting of hydrogen and chloride. $R_{12}$ is an amine blocking group.

The amino blocking group $R_{12}$ is then removed for deblocking the first C/N-terminal functionalized immobilized fucoside so as to form a second C/N-terminal functionalized immobilized fucoside having a free N-terminal amino group. The N-terminal amino group of the second C/N-terminal functionalized immobilized fucoside is then reacted with an acceptor represented by the formula $R_9COY$ for forming a functionalized immobilized fucoside. $R_9$ of the acceptor is a radical selected from a group consisting of —(CH$_2$)PCO$_2$Bn, and —(CH$_2$)$_p$PO(OBn)$_2$; Y is a radical selected from a group consisting of hydrogen and chloride; $1 \leq p \leq 5$. The functionalized immobilized fucoside represeted by the following structure:

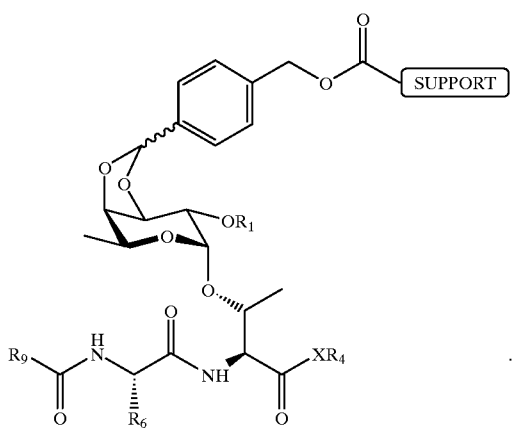

The functionalized immobilized fucoside is then cleaved from the support molecule for forming an advanced intermediate represented by the following structure:

In the above construct, the carbohydrate is linked to the construct by an acetal linkage. The method employs the step of cleaving the acetal for releasing the carbohydrate from the construct.

DETAILED DESCRIPTION OF THE INVENTION

The invention is directed to a parallel and/or combinatorial synthesis of a designed library of O- and C-fucopeptides (3, FIG. 2) structurally related to 2, which is nearly as active at. $sLe^x$ against E-selectin (Wu et al. Angew. Chem. 1996, 108, 106; Angew. Chem. Int. Ed. Engl. 1996, 35, 88).

Figure 1:
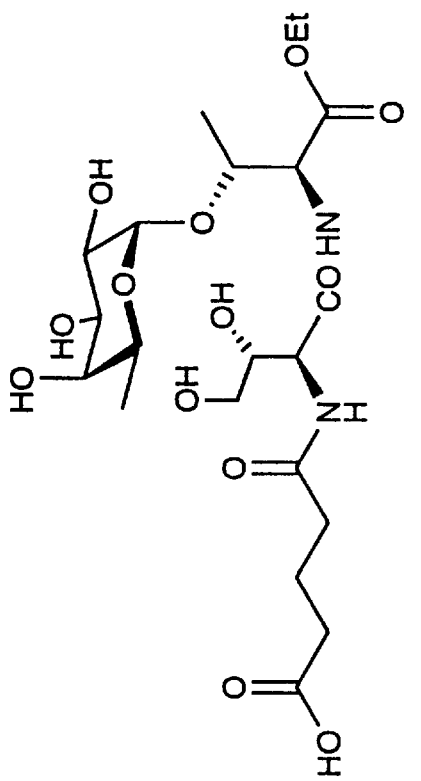
FIG. 1 compares and contrasts the unique structures of tetrasaccharide Sialyl Lewis X 1 and fucopeptide 2, which is an oligosaccharide mimic.
Figure 1:
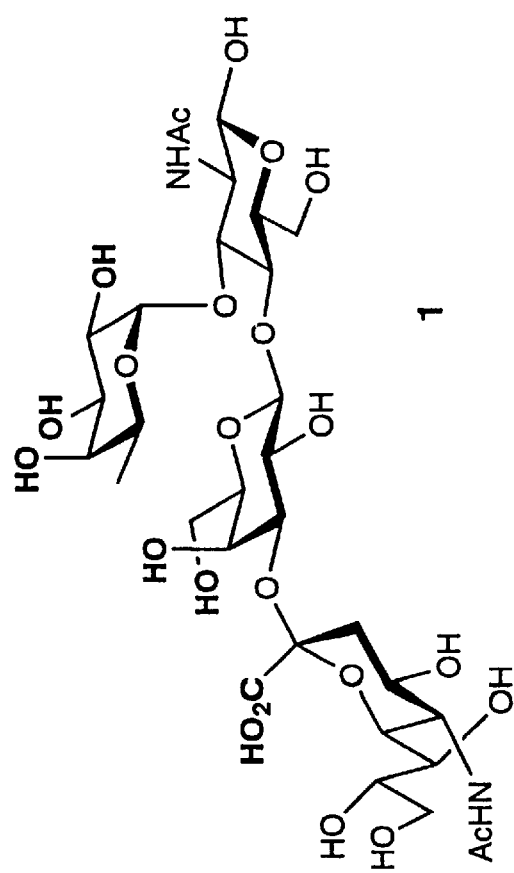
Figure 2:
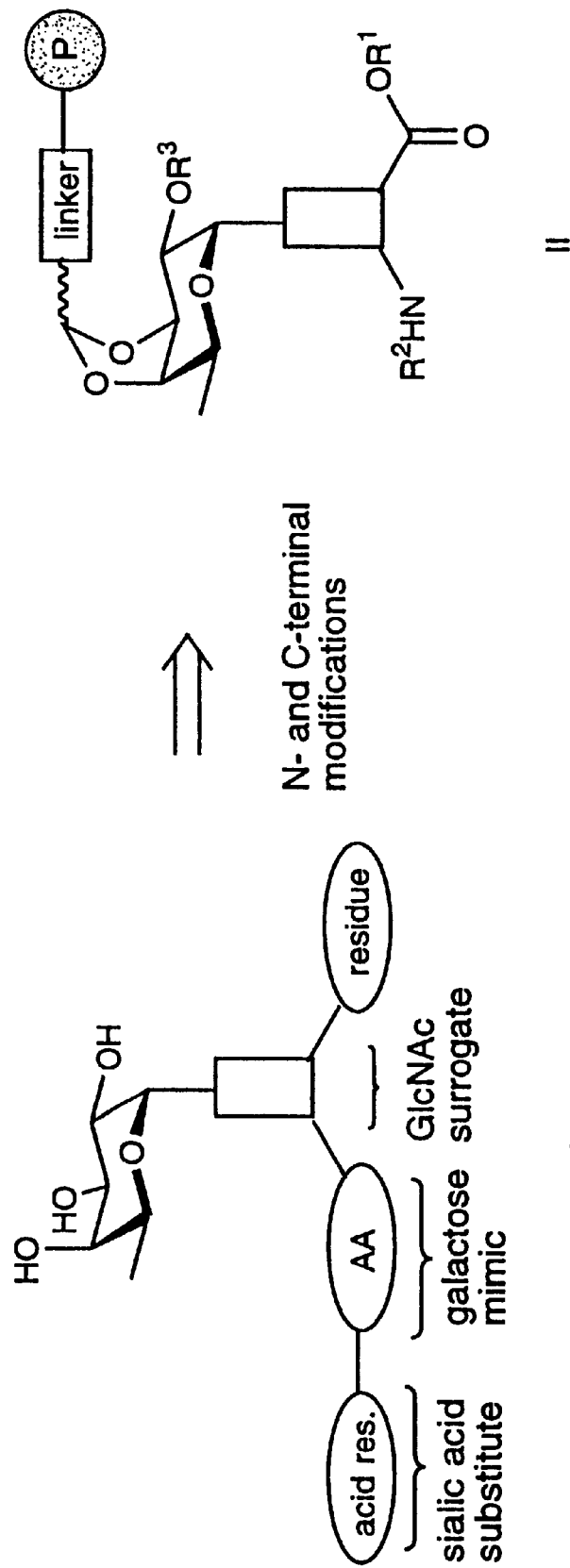
FIG. 2 illustrates the general modular assembly of fucopepetides by bi-directional synthesis on solid phase.

Fucose, containing three hydroxyl groups critical for $sle^x$ reognition by E-selectin, was retained as the only carbohydrate moiety in the mimic, whereas the GlcNAc is replaced by (L)-threonine and its derivatives. Anchoring the fucose GlcNAc surrogate II (FIG. 2) as a core via its 3,4-cis diol unit (Anchoring 1,3- and 1,2-diols onto solid supports has been reported: Frechet et al. J. C. S. Chemi. Comn. 1975, 225; Seymour et al. Tetrahedron Lett. 1976, 3669 Hanessian et al. Carbohydr. Res. 1974, 38, C15; Palom et al. Tetrahedron Lett. 1993, 34, 2195; Wang et al. J. Med. Chem. 1995, 38, 2995) enables the bi-directional functionalization of the glycosylated amino acid while bound to the solid support. N-terminal functionalization allows the elaboration of optimal substitutions for the galactose and sialic acid residues Although C-terminal modified peptide amides and esters are accessible through use of specific linker groups, the approaches reported so far are not adaptable to combinatorial methodologies. More synthetic flexibility has been introduced by the concept of post-synthetic C-N inversion on the solid phase: (Davies et al. Angew. Chem. 1997, 109, 1135; Angew. Chem. Tnt. Ed. Engl. 1997, 36, 1097; Kania et al. J. Am Chem. Soc. 1994, 116, 8835) C-terminal modifications can be used to install additional functionalities to interact new groups in selecting. For increase of binding affinities of sLex derivatives and mimetics through aromatic or hydrophobic interactions with selectins see Ramphal et al. J. Med. Chem. 1996, 39, 1357; Tsujishita et al. ibid., 1997, 40, 362. The use of Fmoc-peptide chemistry and the application of an orthogonal protection strategy ($R^1$=All, $R^2$=Fmoc, $R^3$=Bn) as well as the reversible immobilization of the 3,4-cis diol moiety of fucose via a highly acid labile linker group in this approach ensure the rapid and bi-directional assembly of fucopeptides I (FIG. 2).

Figure 3:
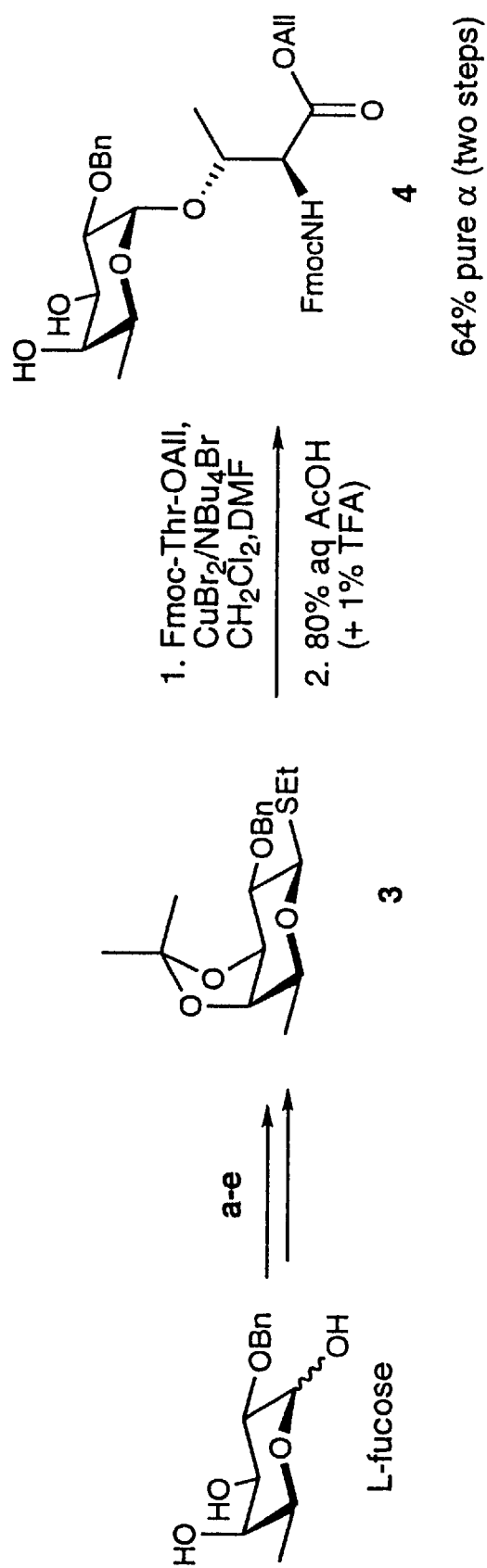
FIG. 3 illustrates the synthesis of compound 4 with the following steps: a) $Ac_2O$, 4-DMAP, pyridine, 0° C. to rt; b) EtSH, $BF_3 \cdot Et_2O$, 0° C. to rt (60%, two steps); c) cat. NaOMe in MeOH, rt; d) 2,2-dimethoxypropane, cat. p-TsOH•$H_2O$, $CH_2Cl_2$, rt (94%, two steps, a/b=1:7); e) NaH, BnBr, cat. tetrabutylammoniumiodide, (TBAI), THF (84%, pure b); f) Fmoc-Thr-OAll, $CuBr_2$/TBAI, $CH_2Cl_2$, DMF; g) 80%, aq. AcOH, (1%, TFA).

The synthesis of orthogonal protected α-fucoside 4 is depicted in FIG. 3. L-fucose was converted to ethyl thiofucoside 3 (5 steps, 47% overall yield) by standard methods known in the art. Using the $CuBr_2$/$NBu_4Br$ protocol (Sato et al. Carbohydr. Res. 1986, 155, C6). Fmoc-protected (L)-threonine allyl ester was glycosylated with 3 to give selectively the α-anomer (α/β~9:1). Upon cleavage of the acetonide with 80% aq. AcOH containing 1% TFA, fucoside 4 was obtained as a single anomer after column chromatography (64% yield, pure α-anomer, two steps).

Figure 4:
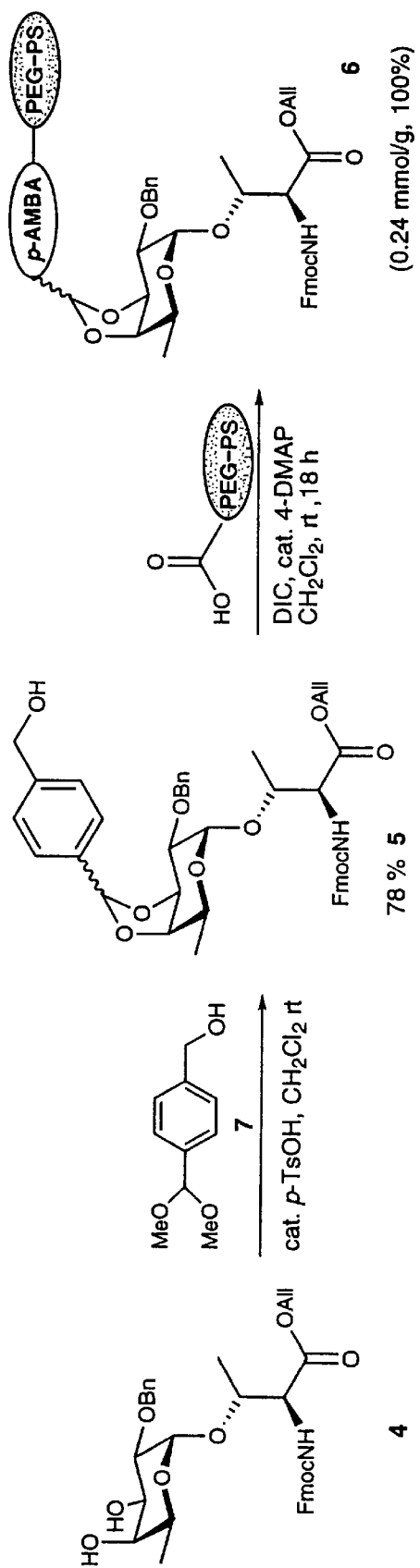
FIG. 4 illustrates the immobilization of fucoside 4 onto a carboxyl functionalized PEG-PS resin via anchor group 7.

Treatment of diol 4 with dimethylacetal 5 and a catalytic amount of p-TsOH•$H_2O$ gave a diastereomeric mixture of benzylidene acetals 6 (FIG. 4). The bifunctional linker 5 was easily derived from commercially available 4-carboxy benzaldehyde by dimethylacetal formation and reduction of the acid residue (62%, two steps). Using a moderate excess (2.1 eq) of alcohol 6 and DIC/4-DMAP activation, 6 was immobilized onto terminally carboxyl functionalized, polyethylene glycol grafted PS resin (PEG-PS) (Bayer, Angew. Chem. 1991, 103, 117; Angew. Chem. Int. Ed. Engl. 1991, 30, 113). The nearly complete recovery of excess of 6 and quantitative loading (0.24 mmol/g) onto the resin render this immobilization procedure particularly useful.

The loading was determined by photometric analysis of Fmoc-deprotection and independently by treating an aliquot of the resin with 80% aq. AcOH (+2% TFA). Diol 4 was liberated quantitatively without any detectable cleavage of the acid sensitive α-fucosidic bond. The combination of the para-acyloxymethyl-benzylidene acetal (p-AMBA) anchor group and PEG-PS solid support performed particularly well to achieve maximal loading, recovery of excess reagent, proper swelling of the solid. support, desirable stability of the acetal linkage during the synthesis and selective cleavage by mild acid as shown in FIG. 4.

Figure 5:
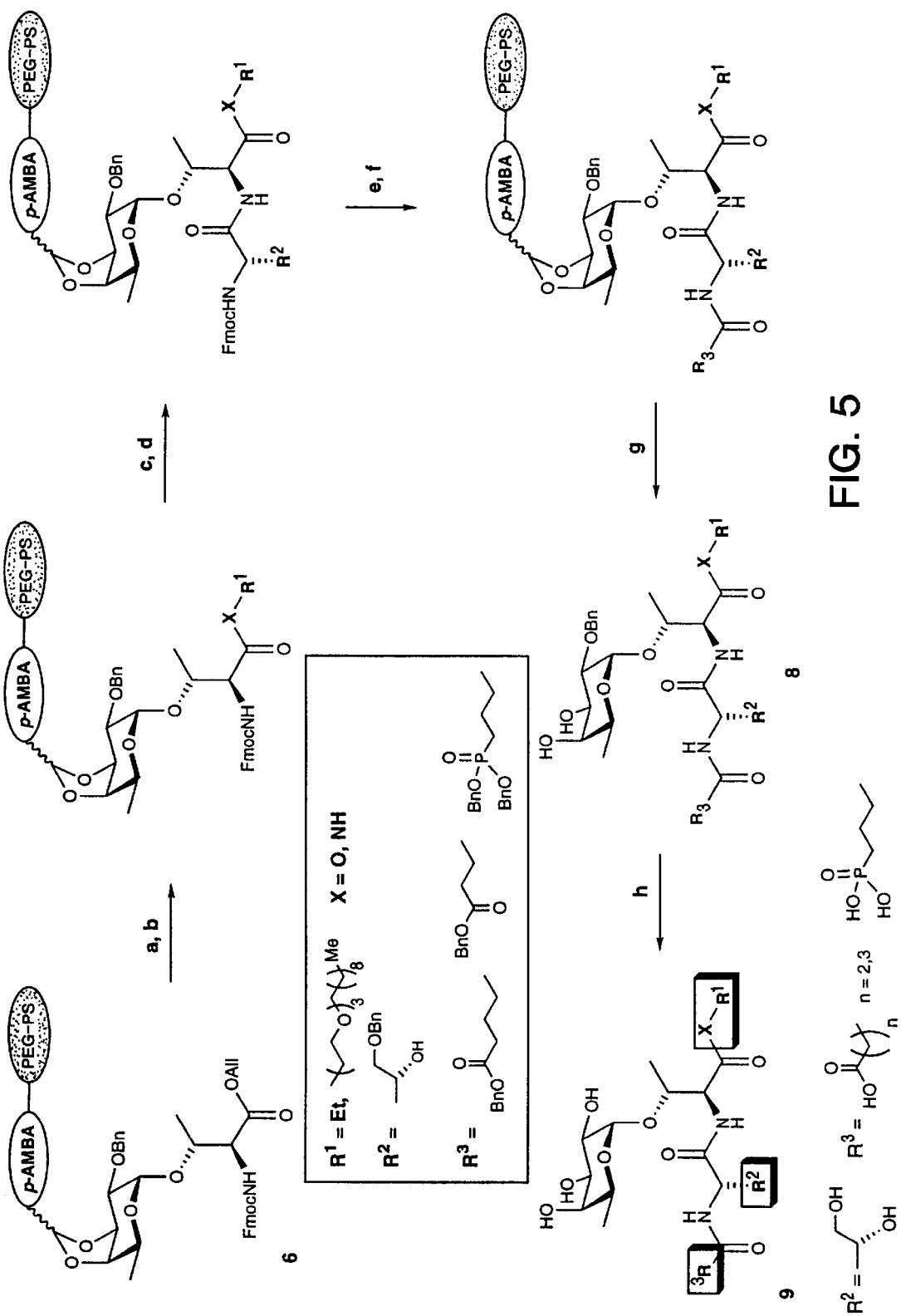
FIG. 5 illustrates the synthesis of compound 8 and intermediates with the following steps: a) cat. $Pd(PPh_3)_4$, dimedone, THF, rt, 18 h; b) cond. A: $R^1OH$, 2,6-dichlorobenzoyl chloride, pyridine, $CH_2Cl_2$/DMF 1:1, rt, 18 h; cond. B: $R^1NH_2$, HBTU, HOBT, NMM, $CH_2Cl_2$/DMF 1:1, rt, 4.5 h; c) DMF/morpholine 1:1, rt, 1 h; d) $FmocNHCHR^2CO_2H$, HBTU, HOBT, NMM, DMF, rt, 4 h; e) DMF/piperidine 3:2, rt, 10 min; f) $R^3CO_2H$, HBTU, HOBT, NMM, DMF, rt, 4 h; g) 2% TFA in 80% aq. AcOH, rt, 2×18–22 h; h) $H_2$, 10% Pd/C, EtOH/THF/$H_2O$, rt, 3–4 h; (definition of $R^1$, $R^2$, and $R^3$ are as defined in the figure).
Figure 6:
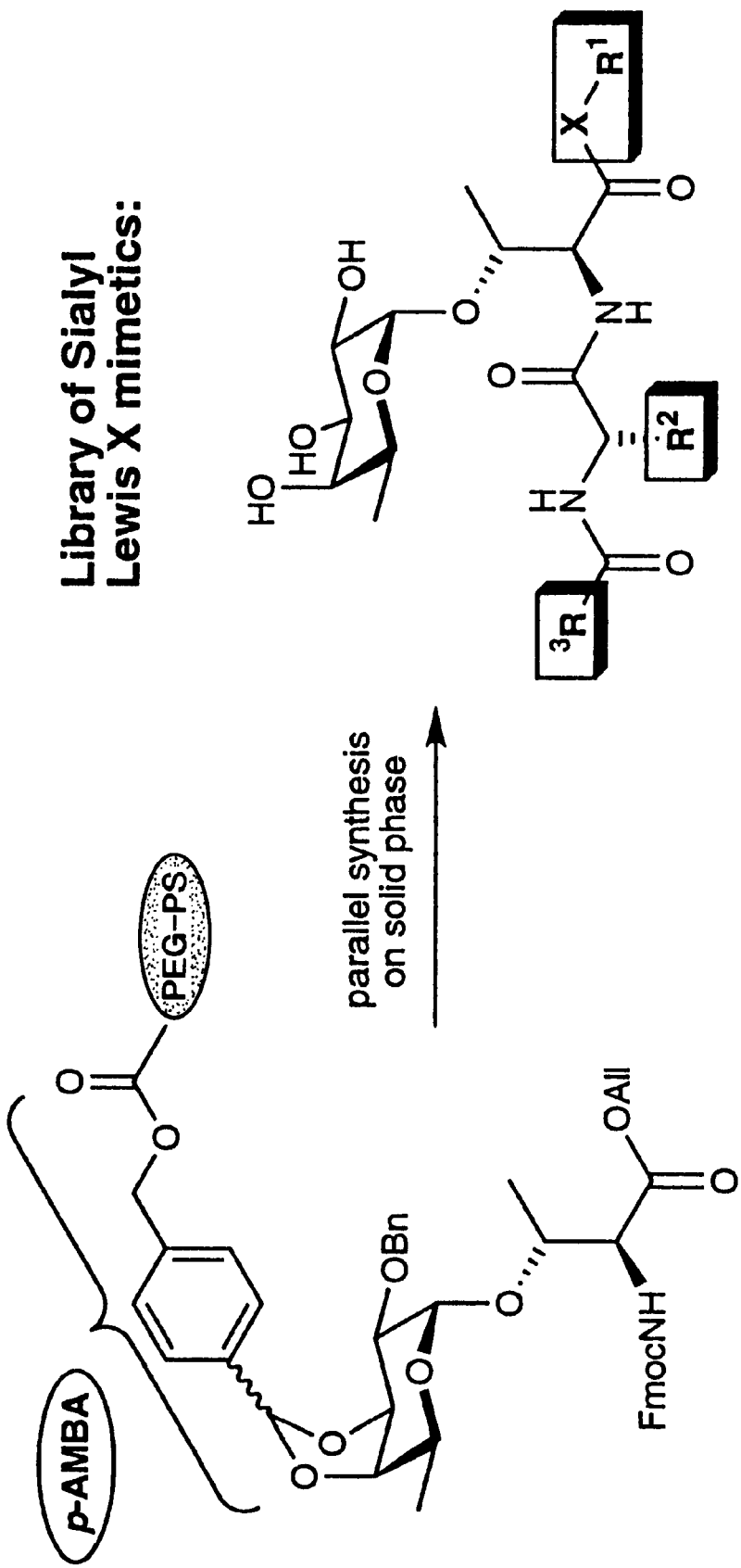
FIG. 6 illustrates the novel anchoring group (para-Acyloxymethylbenzylidene acetal, p-AMBA) which enables the bi-directional functionalization of glycosylated amino acid derivatives and thus the rapid parallel synthesis of fucopeptides as Sialyl Lewis X mimetics on solid phase, leading to the discovery of new mimetics against P-selectin with $IC_{50}$ values in the low mM range.

Starting from 0.8 mmol 6-sp bound to the resin, a parallel synthesis of sLe$^x$ mimetics 8 was conducted on a preparative scale (starting with 0.1 mmol 6-sp per 8, FIG. 5). At branching points of the synthesis the material was separated in dry state by dividing into equal parts.

Allyl isomerization (Kunz et al. *Int. J. Peptide Protein Res.* 1985, 26, 493; Kates et al. *Peptides: Chemistry, Structure & Biology, Proc.* 13th *American Peptide Symposium*, Escom, Leiden, 1994, p. 113) by the action of Pd$^0$ with dimedone as a scavenger liberated the C-terminus of the fucose threonine conjugate 6-sp, which was subsequently modified. The formation of ester bonds was best accomplished with a large excess of alcohol and activation by a mixed anhydride (Sieber et al., *Tetrahedron. Lett.* 1987, 28, 6147) and amide bonds were formed using standard peptide coupling conditions.

Figure 10:
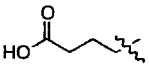
FIG. 10 shows a table of compounds of the family 9a–h wherein in this series $R^2$ remains constant, Fmoc protected γ-benzyloxy (L)-allo-threonine (γ-Benzyloxy (L)-allo-threonine was prepared by L-Threonine Aldolase catalyzed aldol condensation of benzyloxyglyceraldehyde and glycine: Vassilev et al. Tetrahedron Lett. 1995, 36, 4081) was used as amino acid building block; [b]reported yields refer to purified fucopeptides 6; [c]yields refer to purified 9 after fractional precipitation of crude hydrogenation products from MeOH/$Et_2O$ (entries -a to -f), ion exchange chromatography (entries -g and -h) and lyophilizing from $H_2O$. The activities were measured according to the procedure described previously using $sLe^a$-polyacrylamide conjugate (The values are an average of three measurements, ±10%.; $IC_{50}$ for $sLe^x$=0.8 mM against E-selectin and >3 mM against P-selectin). Assays were done according to the procedures by G. Weitz-Schmidt et al. Analytical Biochem. 1996, 238, 184; All compounds were active against P-selectin with $IC_{50}$ values ranging from 1 to 7 μM using sLea-polylysine conjugate assay: Thoma et al. J. Am. Chem. Soc. 1997, 119, 7414.
Figure 10:
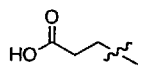
Figure 10:
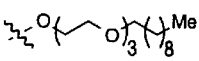
Figure 10:
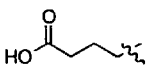
Figure 10:
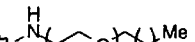
Figure 10:
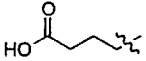
Figure 10:
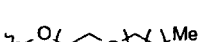
Figure 10:
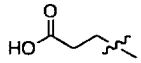
Figure 10:
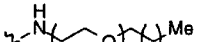
Figure 10:
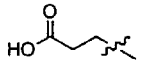
Figure 10:
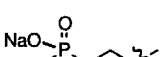
Figure 10:
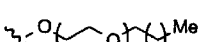
Figure 10:
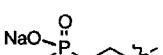

Our model studies revealed that, the C-terminal functionalization on solid phase proved to be high yielding with no racemization. Manual peptide synthesis by established Fmoc-cleavage and amino acid coupling protocols followed by mild acid induced cleavage of the anchoring benzylidene acetal afforded protected fucopeptides 8 in high yields (see table of FIG. 10). Compounds derived from diketopiperazine formation or cleavage of the α-fucosidic bond were not detected during analysis of crude cleavage products by mass spectroscopy.

Figure 7:
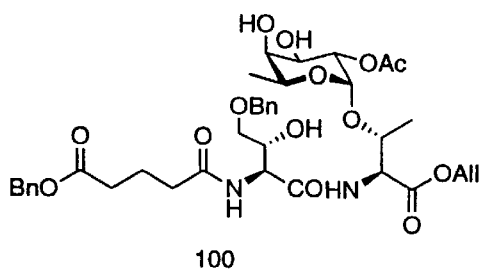
FIG. 7 illustrates new mimetics (100–700), some of which have activity against P-selectin with $IC_{50}$ values in the low mM range.
Figure 7:
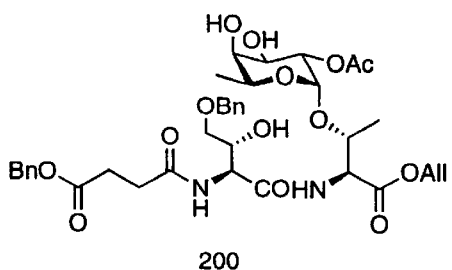
Figure 7:
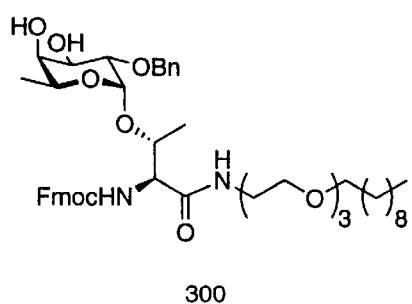
Figure 7:
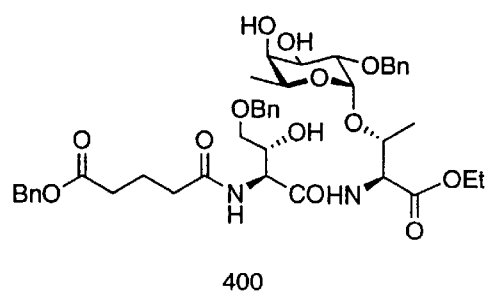
Figure 7:
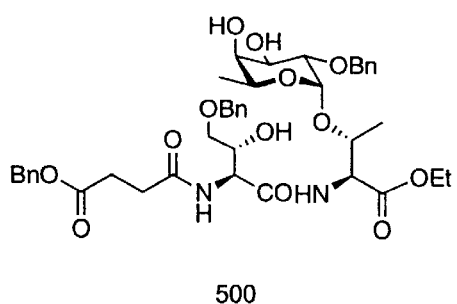
Figure 7:
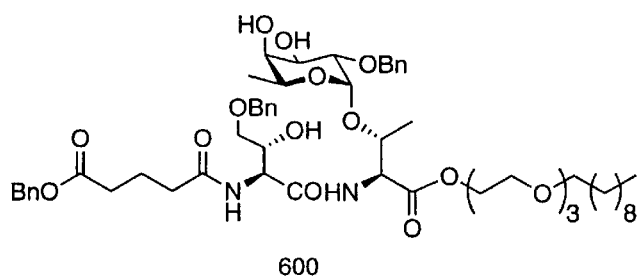
Figure 7:
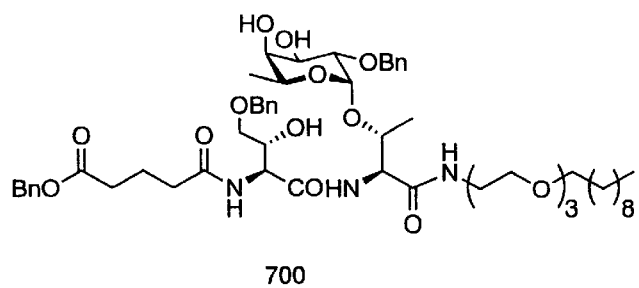

In order to obtain homogeneous materials for biological evaluation, fucopeptides 8 were chromatographed on silica gel. Yields for 8 range from 47 to 65% (based on initial loading), corresponding to an average yield of 90 to 94% per step. Removal of benzylic protecting groups by catalytic hydrogenation afforded final mimetics 9 as illustrated in FIG. 5 and FIG. 7.

Fucopeptides 9a–h were tested against E- and P-selectins in a cell-free assay system (Weitz-Schmidt et al. *Analytical Biochem.* 1996, 238, 184). All compounds were active against P-selectin with IC$_{50}$ values ranging from 1 to 7 μM using sLea-polylysine conjugate assay under the conditions of Thoma et al. *J. Am. Chem. Soc.* 1997, 119, 7414) Using polyvalent sLe$^a$ attached to a polyacrylamide in the E-selectin assay, all members of the fucopeptide library showed only moderate binding affinities, with phosphonate fucopeptide 9-h being the most active representative (IC$_{50}$= 0.7 mM).

While the biological activity of the tested fucopeptides against E-selectin decreased with a long-chain C-terminal residue (XR$^1$), the opposite was observed for the library in the P-selectin assay: Binding affinity generally increased significantly by addition of a triethyleneglycol decylether residue (ester or amide linkage). Ester derivative 9-c binds 53 times better than ethyl derivative 9-a. An increase of biological activity is also observed for the corresponding amide 9-d, as it binds 100 times better (compared to 9-a).

The influence of N-terminal residue R$^3$ on binding to P-selectin seems to be limited, with phosphonate fucopeptide 9-h (IC$_{50}$=17 μM) being the most active member of the library against P-selectin. Comparing inhibition values for both selectins, fucopeptides 9-d (~100 fold) and 9-h (almost ~200 fold) exhibit significantly better inhibition of P- vs. E-selectin, thus they represent sLe$^x$ mimetics with a remarkable selectivity profile towards inhibition of P-selectin.

In conclusion, we have inventoed a new synthetic strategy for the parallel synthesis of fucopeptides as sLex mimetics on solid phase. Linking the sugar via a highly acid sensitive 1,2-diol protecting and anchoring group (p-AMBA) enables the variation in functionalization of the N- and C-terminal of glycopeptides. Thus, access to a library of sLex mimetics by parallel or combinatorial synthesis can be obtained and a rapid optimization of the biological activity of a known lead structure has been achieved. Some members of the synthesized fucopeptide library exhibited high selectivity and activity against P-selectin in cell-free assay systems. Work is in progress to test the versatility of p-AMBA based immobilization methodology in other synthetic areas involving 1,2- and 1,3-diol units, e.g. the synthesis of complex oligosaccharides on solid phase

EXPERIMENTAL PROTOCALS

General:

$^1$H and $^{13}$C. nmr spectra were recorded either on a Bruker AM-250, a Bruker AMX-400 or a Bruker AMX-500 spectrometer. Residual protic solvent CHCl$_3$ ($\delta_H$=7.26 ppm, $\delta_c$=77.0), d$_4$-methanol ($\delta_H$=3.30 ppm, $\delta_c$=49.0) and D$_2$O ($\delta_H$=4.80 ppm, $\delta_c$ (of CH$_3$CN)=1.7 ppm) or TMS ($\delta_H$=0.00 ppm) were used as internal reference. Coupling constants were measured in Hertz (Hz). HRMS were recorded using FAB method in a m-nitrobenzylalcohol (NBA) matrix doped with NaI or CsI. Infra-red spectra were recorded on a Perkin-Elmer FTIR 1620 spectrometer. Enantiomeric excess was determined by HPLC using a Daicel Chemical Industries CHIRALPAK AD column. Optical rotations were measured with an Optical Activity AA-1000 polarimeter. Melting points were taken on a Thomas Hoover capillary melting point apparatus and are uncorrected. Column chromatography was performed on Merck Kieselgel 60 (230–400 mesh). Analytical thin layer chromatography was performed using pre-coated glass-backed plates (Merck Kieselgel F$_{254}$) and visualized by cerium molybdophosphate or ninhydrin. Diethyl ether, tetrahydrofuran (THF) and toluene (PhCH$_3$) were distilled from sodium-benzophenone ketyl, dichloromethane (DCM) and acetonitrile from calcium hydride. Other solvents and reagents were purified by standard procedures if necessary.

γ-Benzyloxy (L)-allo-threonine

γ-Benzyloxy (L)-allo-threonine was prepared by L-Threonine Aldolase catalyzed aldol condensation of benzyloxyglyceraldehyde and glycine: Vassilev et al. *Tetrahedron Lett.* 1995, 36, 4081.

Immobilization of 6 as illustrated in FIG. 5 (SEE GENERAL PROCEDURE BELOW)

After drying 3.85 g (0.26 mmol/g, 1.0 mmol on resin) of carboxyl functionalized resin for several hours under high vacuum, 4-DMAP (12.2 mg, 0.1 mmol) and a solution of alcohol 6 (1.545 g, 2.1 mmol) in dry CH$_2$CL$_2$ (16 ml) were added and the suspension was gently shaken for 14 h at rt. The reaction mixture was transferred into a peptide synthesis vessel, filtered and after washing thoroughly with dry $CH_2Cl_2$, the resin was dried under high vacuum to give 4.32 g of material. The combined filtrate was concentrated in vacuo and the unreacted alcohol 6 (740 mg, 1.0 mmol, 48%) was recovered after purification by column chromatography on silica gel. Fmoc-cleavage of dry resin followed by photometric analysis revealed a loading of ~0.24 mmol/g (~1.04 mmol on resin, 100% functionalization). Fmoc-cleavage and amino acid coupling. After swelling in DMF and removal of DMF, the resin was suspended (0.6 ml solvent per 100 mg of dry resin) in a 1:1 mixture of DMF/morpholine (step c, scheme 4) and shaken for 1 h at rt or suspended in 3:2 mixture of DMF/piperidine (step e, scheme 4) and shaken for 10 min at rt. After washing with dry DMF (6 times each with 1 ml per 100 mg dry resin), a pre-stirred (5–10 min) solution of the acids used for coupling (3 eq for step d and 6 eq for step f, scheme 4), HOBT, NMM and HBTU (1.6 eq, 2.2 eq and 1.05 eq, refers to the amount of acid) in dry DMF (0.2–0.25 molar in acid) was added to the resin After shaking for 4–4.5 h at rt, the coupling reaction was terminated by filtration and the solution was washed with DMF and $CH_2Cl_2$ (6 times each). Cleavage from the resin. A suspension of resin in 80% aq. AcOH (0.9 ml per 100 mg dry resin) containing 2%; TFA was shaken for 18–22 h at rt. After filtration and washing 3 times with 80% aq. AcOH, the cleavage procedure was repeated once. The filtrate was concentrated in vacuo and residues of AcOH and $H_2O$ were removed by coevaporating two times with dry toluene. The colorless to slightly yellow oil or solid was purified by column chromatography on silica gel to afford homogeneous material by HR-MS, 1H and 13C NMR.

General Synthesis of fucopeptides on a solid phase as illustrated in FIG. 5

1) allyl isomerization

Resin containing a solid phase bound allyl ester was placed in a peptide synthesis vessel and washed with dry THF under argon. Dimedone (6.0 eq) and dry THF (8 ml/g resin) were added and the suspension was agitated for 5 min by bubbling argon through. $Pd(PPh_3)_4$ (0.25 eq) was added while argon bubbling was continued. After 5 min the suspension was protected from light and gentle shaken at rt for 18 h, before the yellow mixture was filtered, washed successively with THF (8 ml/g resin), 1% solution of NMM in DMF (2x, 6 ml/g resin), 0.5% solution of Sodium dithiodiethylcarbamate in DMF (2x, 6 ml/g resin), DMF (2x, 6 ml/g resin) and $CH_2Cl_2$ (4x 6 ml/g resin). After drying at high vacuum the resin could be further partionated.

2) C-terminal functionalization:

a) ester bond formation: The resin bound free carboxylate (~0.24 mmol/g) was suspended in anhydrous $CH_2Cl_2$ (2 ml/g resin) and anhydrous DMF (2 ml/g resin) in dry RBF under argon. Dry alcohol (10 eq) and dry pyridine (20 eq) were added and the mixture was shaken gentle for 5 min, before 2,6-dichlorobenzoyl chloride (7.5 eq) was added. Gentle shaking of the suspension was then continued over night at rt. The heterogeneous mixture was transferred into peptide synthesis vessel and the resin was washed six times with dry $CH_2Cl_2$ (5 ml/g resin) and then dried at high vacuum.

b) amide bond formation: The resin bound free carboxylate (~0.24 mmol/g) was suspended in anhydrous DMF in a peptide synthesis vessel. The solvent was removed by filtration and HOBT (2.5 eq), NMM (3.5 eq) and dry $CH_2Cl_2$ (1.6 ml/g resin) were added. After addition of dry DMF (0.8 ml/g resin), the resin was shaken gentle for 5 min, before HBTU (1.8 eq) was added. After shaking for 5 min, the amine (3 eq, could be reduced to 2 eq) was added and gentle shaking of the resin was continued for 4.5 h at rt. The solvents were removed by filtration and the resin was washed six times with dry DMF (4 ml/g resin).

3) Fmoc-cleavage and amino acid coupling:

After swelling in DMF and removal of DMF, the resin was suspended (0.6 ml/100 mg of dry resin) in a 1:1 mixture of DMF/Morpholine (for removal of Fmoc from the first amino acid) and shaken for 1 h at rt or suspended in 3:2 mixture of DMF/Piperidine (for removal of Fmoc from the second amino acid) and shaken for 10 min at rt. After washing with dry DMF (6 times each with 1 ml/100 mg dry resin), a pre-stirred (5–10 min) solution of the acids used for coupling (3 eq for the second amino acid and 6 eq for the third acid residue), HOBT, NMM and HBTU (1.6 eq, 2.2 eq and 1.05 eq, refers to the amount of acid) in dry DMF (0.2–0.25 molar in acid) was added to the resin. After shaking for 4–4.5 h at rt, the coupling reaction was terminated by filtration and washing with DMF and $CH_2Cl_2$ (6 times each). After drying at high vacuum the resin could be further partionated 4) Cleavage from the resin:

A suspension of resin in 80% aq. ACOH (0.9 ml/100 mg dry resin) containing 2% TFA was shaken for 18–22 h at rt. After filtration and washing three times with 80 aq. AcOH the cleavage procedure was repeated once. The filtrates were concentrated in vacuo and rests of AcOH and $H_2O$ were removed by coevaporating 2 times with dry toluene. The colorless to slightly yellow oil or solid was purified by column chromatography on silica gel to afford homogeneous material.

General hydrogenation yielding final mimetics as illustrated in FIG. 5

Benzyl protected fucopeptides were dissolved in a mixture of $EtOH/THF/H_2O$ (5:1:1), 10% Pd/C as hydrogenation catalyst was added and the suspension was purged several times with hydrogen. Vigorous stirring under $H_2$ (1 atm) was continued for 3–4 h. The mixture was filtered through celite (washed with EtOH or $EtOH/H_2O$) and concentrated in vacuo. case a) carboxylates: the residual colorless oil or solid was dissolved in MeOH and fractional precipitated by addition of $Et_2O$. The precipitate was collected and lyophilized from $H_2O$ to afford the deprotected fucopeptides; case b) phosphonates: before concentration 3 eq of Triethylammonium hydrogen carbonate (1M solution in $H_2O$) were added. Exchange of the counterion to sodium was performed by ion exchange/size exclusion chromatography (sephadex, eluent $H_2O$) to give after lyophilizing phosphonate mimetics as colorless solids.

Synthesis and immobilization of compound 5 as illustrated in FIG. 4

After drying 3.85 g (0.26 mmol/g, 1.0 mmol on resin) of carboxyl functionalized resin for several hours under high vacuum, 4-DMAP (12.2 mg, 0.1 mmol), DIC (1.5 mmol) and a solution of alcohol 5 (1.545 g, 2.1 mmol) in dry $CH_2Cl_2$ (16 ml) were added and the suspension was gently shaken for 14 h at rt. The reaction mixture was trans-ferred into a peptide synthesis vessel, filtered and after washing thoroughly with dry $CH_2Cl_2$, the resin was dried under high vacuum to give 4.32 g of material. The combined filtrate was concentrated in vacuo and the unreacted alcohol 5 (740 mg, 1.0 mmol, 48%) was recovered after purification by column chromatography on silica gel. Fmoc-cleavage of dry resin followed by photometric analysis revealed a loading of ~0.24 mmol/g (~1.04 mmol on resin, 100% functionalization).

General procedures: Fmoc-cleavage and amino acid coupling

After swelling in DMF and removal of DMF, the resin was suspended (0.6 ml solvent per 100 mg of dry resin) in a 1:1 mixture of DMF/morpholine (step c, scheme 4) and shaken for 1 h at rt or suspended in 3:2 mixture of DMF/piperidine (step e, scheme 4) and shaken for 10 min at rt. After washing with dry DME (6 times each with 1 ml per 100 mg dry resin ), a pre-stirred (5–10 min) solution of the acids used for coupling (3 eq for step d and 6 eq for step f, scheme 4), HOBT, NMM and HBTU (1.6 eq, 2.2 eq and 1.05 eq, refers to the amount of acid) in dry DMF (0.2–0.25 molar in acid) was added to the resin. After shaking for 4–4.5 h at rt, the coupling reaction was terminated by filtration and the resin was washed with DMF and $CH_2Cl_2$ (6 times each).

General procedures: cleavage from the resin

A suspension of resin in 80% aq. AcOH (0.9 ml per 100 mg dry resin) containing 2% TFA was shaken for 18–22 h at rt. After filtration and washing 3 times with 80% aq. AcOH, the cleavage procedure was repeated once. The filtrate was concentrated in vacuo and residues of AcOH and $H_2O$ were removed by coevaporating two times with dry toluene. The colorless to slightly yellow oil or solid was purified by column chromatography on silica gel to afford homogeneous material by HR-MS, $^1H$ and $^{13}C$ NMR. Data for selected compounds: 9b, colorless hygroscopic solid: $^1H$ NMR (500 MHz, $D_2O$): d=4.95 (d, J=3.5 Hz, 1 H), 4.68 (s,br, 1 H), 4.54 (d, J=7.2 Hz, 1 H), 4.44 (q, J~6.1 Hz, 1 H), 4.22 (dq, J=10.6, 7.2 Hz, 1 H), 4.12 (dq, J=10.6, 7.2 Hz, 1 H), 3.97 (m, 1H), 3.74–3.69 (m, 5 H), 3.60 (dd, J=12.1, 6.4 Hz, 1 H), 2.62–2.52 (m, 4 H), 1.24 (t, J=7.1 Hz, 3 H), 1.15 (d, br, J~6.4 Hz, 6 H); HR-MS for $C_{20}H_{34}O_3N_2Cs$, $(M+Cs)^+$: calcd 643.1115, found 643.1139. 9d, colorless hygroscopic solid: $^1H$ NMR (500 MHz, $D_2O$) d=4.94 (d, J=3.7 Hz, 1 H), 4.53 (d, J=9.0 Hz, 1 H), 4.44 (s, br, 1H), 4.41 (d, J=6.3 Hz, 1 H), 3.89–3.87 (m, 1 H), 3.75–3.52 (m, 16 H), 3.43 (t, J=6.7 Hz, 2 H), 3.31–3.36 (m, 2 H), 2.29 (t, J 7.1 Hz, 2 H), 2.24 (t, J=7.4 Hz, 2 H), 1.81 (t, J~7.3 Hz, 2 H), 1.55–1.50 (m, 2 H), 1.28–1.21 (m, 14 H), 1.18 (d, J=6.1 Hz, 3 H), 1.14 (d, J=6.4 Hz, 3 H), 0.83 (t, br, J~6.6 Hz, 3 H); HR-MS for $C_{35}H_{65}O_{15}N_3Cs$, $(M+Cs)^+$: calcd 900.3470, found 900.3498. 9-e, colorless hygroscopic solid: $^1H$ NMR (500 MHz, $D_2O$): d=4.94 (d, J=3.5 Hz, 1 H), 4.70 (s, br, 1 H), 4.58 (d, J=7.2 Hz, 1 H), 4.42–4.35 (m, 2 H), 4.18–4.16 (m, 1 H), 3.97–3.96 (m, 1 H), 3.74–3.55 (m, 16 H), 3.42 (t, J=6.5 Hz, 2 H), 2.64–2.53 (m, 4 H), 1.53 (s, br, 2 H), 1.30–1.23 (m, 14 H), 1.17 (d, J=6.1 Hz, 3 H), 1.15 (d, J=6.4 Hz, 3 H), 0.85 (t, br, J~6.5 Hz, 3 H); HR-MS for $C_{34}H_{62}O_{16}N_2Cs$, $(M+Cs)^+$: calcd 887.3154, found 887.3184.

Synthesis of Ethyl 2,3,4-tri-O-acetyl-1-thio-β-L-fucopyranoside as illustrated in FIG. 3 (Steps a–b)

To an ice cooled suspension of (L)-fucose (16.42 g, 100 nmol) and 4-DMAP (610 mg, 5 mmol) in dry pyridine (40 ml) was added acetic anhydride (45.3 ml, 480 mmol) over a period of 15 min. The reaction mixture was stirred for 5 h at rt, then diluted with $Et_2O$ and washed successively with $H_2O$, 4 x 1N HCl, 3x sat. $NaHCO_3$ and brine. The organic layer was dried over $MgSO_4$, concentrated in vacuo and coevaporated with dry toluene to remove rests of pyridine. The residual oil was dissolved in dry $CH_2Cl_2$ (40 ml) and transferred into a slurry of flame dried 4 Å molecular sieves (33 g) in 50 ml of dry $CH_2Cl_2$. Ethane thiol (22.2 ml, 300 mmol) was added and the suspension was cooled to −15° C.. Over a period of 30 min $BF_3*Et_2O$ (76 ml, 600 mmol) was added and vigoruos stirring was continued over night while the mixture was allowed to warm up to rt. The suspension was filtered through celite (thoroughly washed with $Et_2O$) and the filtrate was carefully poured on sat. $NaHCO_3$. The aqueous layer was reextracted with $Et_2O$ and the combined organic layers were washed with sat. $NaHCO_3$ and brine, dried over $MgSO_4$ and concentrated in vacuo. The crude product was purified by column chromatography (600 g silica gel, $Hex/Et_2O$ 2:1 to 2:3) to afford 20.14 g of a mixture of a/β-anomers (1:6.9) as a slightly yellow solid (60.2 mmol, 60%) The anomers can be seperated by column chromatography (one a smaller scale the yield increased to 60% for β- and 9% for the α-anomer).

Synthesis of ethyl 3.4-isopropylidene-1-thio-β-L-fucopyranoside as illustrated in FIG. 3 (steps c–d)

To a solution of 2,3,4-triacetyl fucoside (20.14 g, 60.2 mmol) in dry MeOH (100ml) was added a solution of NaOMe (1.2 ml, 25%). After stirring at rt for 2.5 h the mixture was neutralized by addition of acidic resin, the material was filtered (thorough washing with MeOH) and the filtrate was concentrated in vacuo. The residue was dried over night at high vacuum, taken up in dry $CH_2Cl_2$ (300 ml) and treated with 2,2-dimetheoxy propane (14.8 ml, 120 mmol) and p-$TsOH.H_2O$ (570 mg, 3 mmol). After stirring for 40 min the reaction mixture was poured on sat. $NaHCO_3$. The aqueous layer was extrated 2x with $Et_2O$, the combined organic layers were washed with brine, dried over MgSO4 and concentrated in vacuo to yield 14.08 g of a highly viscous oil (α/β1;7, 56.7 mmol, combined yield 94%). The anomeric fucosides can be seperated by chromatography to give pure β-anomer (84% yield)

Synthesis of 3,4-isopropylidene-2-O-benzyl-1-thio-β-(L)-fucopyranoside (3) as illustrated in FIG. 3

To an ice cooled solution of intermediate alcohol (from step d, above: 4.47 g, 18 mmol) in 20 ml of dry DMF was added NaH (568 mg, 95%, 22.5 mmol) followed by benzyl bromide (2.8 ml, 23.4 mmol). After 5 min TBAI (133 mg, 0.36 mmol) and more dry DMF (5 ml) were added and the thick suspension was allowed to warm up to rt over night. The reaction mixture was quenched with 1N HCl and diluted with EtOAc. The organic layer was washed with sat. $NaHCO_3$ and brine, dried over $MgSO_4$ and concentrated in vacuo. The crude product was purified by flash chromatography to afford 5.16 g of a slightly yellow oil (13.2 mmol, 84%) $^1H$ NMR (400 MHz, $CDCl_3$) d 7.44–7.24 (m, 5 H), 4.85 (d, J=11.4, 1 H), 4.76 (d, J=11.4, 1 H) 4.39 (d, J=8.9, 1 H), 4.19 (dd, J=6.6, 5.7, 1 H), 4.05 (dd, J=5.6, 2.2, 1 H), 3.81 (dq, J=6.6, 2.1, 1 H), 3.44 (dd, J=9.8, 6.7, 1 H), 2.79–2.63 (m, 2 H), 1.45 (s, 3 H), 1.39 (d, J=6.6, 3 H), 1.36 (s, 3 H), 1.29 (t, J=7.4, 3 H); $^{13}C$ NMR (100 MHz, $CDCl_3$) d 137.65, 127.99, 127.91, 127.36, 109.18, 82.99, 79.44, 78.67, 76.19, 73.10, 27.71, 26.11, 24.05, 16.51, 14.58; HRMS calcd for $C_{18}H_{26}O_4S,Na=(M+Na)^+$361.1450, found 361.1462.

Synthesis of N-(9-Fluorenylmethoxycarbonyl)-a-L-fucopyranosyl)-(L)-threonine allyl ester (4) as illustrated in FIG. 3

Step A) From 2-O-MPM protected acetonide: A solution of fucoside 3 (3.472 g, 5.05 mmol) in $CH_2Cl_2$ (25 ml)

containing H$_2$O (2.5 ml) was cooled to 0° C. and treated with CAN (5.814 g, 10.6 mmol). After 15 min the cooling bath was removed and stirring was continued for 30 min, before the orange suspension was diluted with EtOAc and poored onto sat. NaHCO$_3$. The aqueous layer was reextracted several times with EtOAc and the combined organic layers were washed with a small amount of brine, dried over Na$_2$SO$_4$ and concentrated in vacuo. The crude mixture was separated by column chromatography (180 g silica gel, Hex/EtOAc 1:20 to pure EtOAc) to yield a colorless foam (1.611 g, 3.06 mmol, 61%). From 2-O-TBS protected acetonide: An ice cooled solution of fucoside intermediate (150 mg, 0.22 mmol) in 2 ml of CH$_3$CN was treated with 100 ml of HF (48%) in 0.2 ml of CH$_3$CN. The cooling bath was removed and stirring was continued for 3 h, before EtOAc and sat. NaHCO$_3$ were added to the heterogeneous mixture. The organic layer was washed with sat. NaHCO$_3$ and brine, dried over MgSO$_4$ and concentrated in vacuo. The residue was chromatographed (16 g silica gel, Hex/EtOAc 1:20 to pure EtOAc) to yield 72 mg of a colorless foam (0.136 mmol, 62%). $^1$H NMR (400 MHz, CDCl$_3$, compound shows rotamers ~1.4:1 in the NMR) d 7.73–7.19 (m, 8 H), 6.85 (d, J=9.7, 0.54 H*), 5.92–5.84 (m, 1 H), 5.52 (s, br, 0.38 H*), 5.34–5.29 (m, 2 H), 4.94 (d, J=3.6, 1 H), 4.90 (d, J=3.6, 1 H), 4.70–4.60 (m, 1 H), 4.57–4.49 (m, 2 H), 4.43–4.35 (m, 2 H), 4.24–4.12 (m, 2 H), 3.94–3.63 (m, 5 H), 3.47 (s, br, 1 H), 1.21–1.11 (m, 6 H); $^{13}$C NMR (100 MHz, CDCl$_3$, rotamers in a ratio of 1:1) d 170.73/170.43, 157.1-/156.96, 143.82/143.61, 143.68/143.56, 143.13, 131.23, 127.57, 126.99/126.91, 125.07, 124.69, 124.61, 119.85, 119.13, 95.35/94.26, 72.11/71.53, 70.64, 70.23/69.19, 68.35/68.19, 67.36/67.01, 66.85/66.56, 66.18/66.13, 59.51/59.93, 47.0/46.89, 16.25/16.19, 14.69/14.62; HRMS calcd for C$_{28}$H$_{33}$O$_9$N$_1$Cs=(M+Cs)$^+$550.2053, found 550.2068.

Step B) To a slurry of flame dried 4 Å molecular sieves (15 g) in dry CH$_2$Cl$_2$ (20 ml) was added a solution of thioglycoside 59 (4.37 g, 12.9 mmol) and Fmoc-Thr-OAll (3.51 g, 9.2 mmol) in dry CH$_2$Cl$_2$ (20 ml) and dry DMF (8 ml). The mixture was stirred for 5 min, before Bu$_4$NBr (1.16 g, 3.6 mmol) and after 5 min dry CuBr$_2$ (4.02 g, 18 mmol) were added. The suspension was protected from light and stirring was continued for 36 h, before the dark reaction mixture was filtered through celite (thoroughly washed with EtOAc). The filtrate was diluted with more EtOAc and washed with sat. NaHCO$_3$ and brine (2x), dried over MgSO$_4$ and concentrated in vacuo. The crude product was chromatographed (400 g silica gel, Hex/Et$_2$O 10:7) to afford 5.98 g of a colorless foam. $^1$H NMR analysis showed ~80% purity for the desired a-anomer (a/b ratio of 9:1 and one additional minor impurity); calc. yield: 7.3 mmol, 79%. Spectroscopic data for a-anomer: $^1$H NMR (400 MHz, CDCl$_3$) d 7.76 (d, J=7.5, 2 H), 7.65–7.61 (m, 2 H), 7.41–7.23 (m, 9 H), 5.96–5.87 (m, 2 H), 5.38–5.24 (m, 2 H), 4.84 (d, J=3.6, 1 H), 4.77 (d, J=12.4, 1 H), 4.73–4.67 (m, 1 H), 4.68 (d, J=12.4, 1 H), 4.60–4.53 (m, 1 H), 4.49–4.35 (m, 4 H), 4.30–4.23 (m, 2 H), 4.11–3.94 (m, 2 H), 3.52 (dd, J=5.6, 2.2, 1 H), 1.42 (s, 3 H), 1.34 (s, 3 H), 1.27 (d, J=6.4, 3 H), 1.24 (d, J=6.3, 3 H); $^{13}$C NMR (100 MHz, CDCl$_3$) d 170.79, 156.78, 143.89, 143.65, 141.21, 138.07, 131.36, 128.39, 127.75, 127.64, 127.02, 125.14, 125.08, 119.90, 118.96, 108.81, 93.77, 75.96, 75.86, 75.24, 72.44, 71.79, 67.21, 66.08, 63.57, 58.81, 47.07, 28.05, 26.24, 16.24, 15.54; HRMS calcd for C$_{32}$H$_{43}$O$_9$N$_1$Cs=(M+Cs)$^+$790.1992, found 790.1920.

Step C) 4.15 g of acetonide formed in step B (~80%, 5.1 mmol) were dissolved in 50 ml of 80% aq. AcOH containing 0.5 ml of TFA. The solution was stirred at rt for 2 h and then concentrated in vacuo. After coevaporation (2x) with toluene the residue was carefully chromatographed (400 g silica gel, Et$_2$O) to afford 2.516 g of a colorless foam 4 (pure α-anomer, 4.1 mmol, 81%). Calculated yield from the glycosylation reaction: 64%, two steps) $^1$H NMR (400 MHz, d$_6$-DMSO) d 7.87 (d, J=7.5, 2 H), 7.72 (d, J=7.3, 2 H), 7.59–7.21 (m, 9 H), 5.93–5.81 (m, 1 H), 5.37–5.33 (m, 1 H), 5.23–5.20 (m, 1 H), 4.86 (d, J=2.9, 1 H), 4.73 (d, J=6.3, 1 H), 4.65–4.53 (m, 5 H), 4.36–4.28 (m, 2 H), 4.23 (t, J=6.9, 1 H), 4.14–4.11 (m, 1 H), 3.79–3.72 (m, 2 H), 3.50 (dd, J=10.0, 2.9, 1 H), 1.10 (d, J=6.2, 3 H), 1.01 (d, J=6.3, 3 H); $^{13}$C NMR (100 MHz, d$_6$-DMSO) d 170.01, 156.60, 143.73, 140.75, 139.22, 132.14, 128.14, 127.71, 127.56, 127.30, 127.13, 125.32, 120.16, 118.15, 94.85, 75.77, 71.92, 71.37, 68.31, 66.27, 66.08, 65.23, 58.72, 46.68, 16.40, 15.98; HRMS calcd for C$_{35}$H$_{39}$O$_9$N$_1$Cs=(M+Cs)+750.1679, found 750.1705.

Synthesis of 4-Hydroxymethylbenzaldehyd dimethylacetal (7) as shown in FIG. 4

To a suspension of 4-carboxybenzaldehyde (7.51 g, 50 mmol) in dry MeOH (40 ml) was added 8 ml (65 mmol) of 2,2-dimethoxypropane and a catalytic amount of p-TsOH.H$_2$O (190 mg, 1 mmol). The suspension cleared, then a colorless precipitate appeared (5 ml of dry MEOH added) and the thick suspension was stirred over night, before 100 mg of NaHCO$_5$ were added and the mixture was concentrated in vacuo. The residue was tho roughly dried at high vacuum, dissolved in dry THF (50 ml) and added dropwise to an ice cooled slurry of LiAlH$_4$ (1.71 g, 45 mmol) in 40 ml of dry THF. After the addition was complete (30 min), the cooling bath was removed and stirring was continued for 5 h, before the reaction mixture was treated with 1N HCl till Al-salts have precipitated (pH 9–10). The organic layer was decanted and the remaining salts were washed several times with Et$_2$O, then treated with H$_2$O/1N HCl and extracted several times with Et$_2$O. All organic layers were combined, washed with brine, dried over MgSO$_4$ and concentrated in vacuo. The crude product was chromatographed (500 g silica gel +0.5% Et$_3$N, Hex/Et2O 2:3) to afford after crystallization from Hex/Et$_2$O 5.66 g 31.1 mmol, 62%) of a colorless, fluffy powder (m.p. 43.5–45° C.). $^1$H NMR (400 MHz, CDCl$_3$) d 7.44 (d, J=8.1, 2 H), 7.36 (d, J=m8.1, 2 H), 5.39 (s, 1 H), 4.69 (d, J=5.9, 2 H), 3.32 (s, 6 H), 1.92 (t, J=5.9, 1 H); $^{13}$C NMR (100 MHz, CDCl$_3$) d 141.10, 137.31, 126.89, 126.73, 102.86, 64.91, 52.61; HRMS calcd for C$_{10}$H$_{14}$O$_3$Na =(M+Na)$^+$205.0841, found 205.0847.

Synthesis of ethyl O-(4-dimethoxyformyl)-benzyl glycolate

To an ice cooled solution of alcohol 7 (456 mg, 2.5 mmol) in dry DMF (5.5 ml) was added NaH (66 mg, 95%, 2.6 mmol) in one portion. The cooling bath removed and the suspension was stirred 45 mn at rt, before the mixture was transferred via canula into a solution of ethyl bromoacetate (554 ml, 5 mmol) in dry DMF (2.8 ml) kept at −25° C. After the addition was complete (15 min) the mixture was further stirred at 0° C. for 15 h, before the reaction mixture was diluted with Et$_2$O, washed with H$_2$O (2x), dried over MgSO$_4$ and concentrated in vacuo. The crude mixture was separated by column chromatography (50 g silica gel, Hex/Et$_2$O 2:1) to afford 172 mg of a colorless oil (0.64 mmol, 26%). $^1$H NMR (400 MHz, CDCl$_3$) d 7.44 (d, J=8.0, 2 H), 7.39 (d, J=8.1, 2 H), 5.39 (s, 1 H), 4.64 (s, 2 H), 4.23 (q, J=7.1, 2 H), 4.09 (s, 2 H), 3.32 (s, 6 H), 1.29 (t, J=7.1, 3 H);

¹³C NMR (100 MHz, CDCl₃) d 170.28, 137.84, 137.31, 127.87, 126.83, 102.85, 72.98, 67.20, 60.86, 52.63, 14.17; HRMS calcd for $C_{14}H_{24}O_5Na=(M+Na)^+$ 291.1208, found 291.1219.

Synthesis of (1-Amino-2,5-dioxa)-octyl decyl ether (10000; FIG. 7) as used in FIG. 5 (R¹ groups: used in step c)

To an ice cooled solution of triethylenglycol monodecylether (940 mg, 3.2 mmol) and dry Et₃N (560 ml, 5.1 mmol) in dry CH₂Cl₂ (9 ml) was added dropwise MeSO₂Cl (335 ml, 4.3 mmol). The cooling bath was removed and the mixture was stirred for 1 h, before the suspension was diluted with EtOAC. The crude mixture was washed with 1N HCl, sat. NaHCO₃ and brine, dried over Na₂SO₄ and concentrated in vacuo. The resulting oil was dissolved in dry DMF (6.4 ml) and NaN₃ was added. The suspension was stirred vigorously for 20 h at 55° C., before diluted with EtOAc. The crude mixture washed with H₂O and brine, dried over Na₂SO₄ and concentrated in vacuo. The resulting colorless oil was purified by column chromatography (65 g silica gel, Hex/Et₂O 10:1 to Hex/EtOAc 1:7) to afford 719 mg of a colorless oil (2.3 mmol, 72%). 679 mg of the azide (2.15 mmol) were dissolved in 10 ml AcOH, the solution was deoxygenated with Argon and 150 mg of Pd(OH)₂/C (20% Pd, Degussa-typ) were added. The suspension was purged several times with H₂ and then stirred vigorously over night under H₂ (1 atm) at rt. The mixture was filtered through Celite, concentrated in vacuo and coevaporated with dry toluene. The residual oil was purified by column chromatography (50 g silica gel, CH₂Cl₂/MeOH 10:1+0.5% Et₃N) to give 443 mg of a yellow oil. The material was further purified by acid/ base washings, dried over Na₂SO₄ and concentrated in vacuo to yield 356 mg of slightly yellow liquid (1.23 mmol, 57%). ¹H NMR (500 MHz, CDCl₃) d 7.68–3.62 (m, 6 H), 3.60–3.58 (m, 2 H), 3.51 (t, 2 H, J=5.2, 2 H), 3.45 (t, J=6.8, 2 H), 2.87 (t, J=5.3, 2 H), 1.61–1.55 (m, 2 H), 1.31–1.29 (m, 14 H), 0.88 (t, J~6.9, 3 H); ¹³C NMR (125 MHz, CDCl₃) d 73.45, 71.54, 70.62, 70.55, 70.28, 70.03, 41.77, 31.86, 29.57, 29.53, 29.45, 2929, 26.05, 22.64, 14.09; HRMS calcd for $C_{16}H_{36}O_3N,C=(M+H)^+$ 290.2695, found 290.2701.

Synthesis of N-(9-Fluorenylmethoxycarbonyl)-y-benzyloxy-(L)-allo-threonine (20000; FIG. 7) used in step d (FmocNHCHR²CO₂H), FIG. 5

To a suspension of y-benzyloxy-(L)-allo-threonine (914 mg, 3.8 mmol) in a mixture of H₂O (6.5 ml) and acetone (6.5 ml) was added NaHCO₃ (336 mg, 4 mmol) and Fmoc-OSuc (1.349 g, 4 mmol). The suspension was stirred vigirously at rt for 24 h, before the pH of the reaction mixture was adjusted to pH ~2 by careful addition of conc. HCl. The suspension was extracted three time with CHCl₃, and the combined organic layers were washed with a small amount of brine, dried over MgSO₄ and concentrated in vacuo. The residual solid was recrystallized from hot CH₂Cl₂ upon addititon of hexane. The precipitate was collected by filtration and afforded after drying at high vacuum a colorless powder (1.437 g, 3.2 mmol, 84%); m.p. 141–142° C. (from CH₂Cl₂/hexanes); ¹H NMR (400 MHz, CDCl₃) d 7.76 (d, J=7.5, 2 H), 7.59 (d, J=7.4, 2 H), 7.40 (t, J=7.4, 2 H), 7.35–7.25 (m, 7 H), 4.55 (s, br, 2 H), 4.49 (d, J=3.9, 1 H), 4.43–4.35 (m, 2 H), 4.23–4.18 (m, 2 H), 3.654 (d, J=5.2, 2 H); ¹³C NMR (100 MHz, CDCl₃) d 171.78, 156.74, 143.68, 143.56, 141.15, 137.43, 128.36, 127.78, 127.71, 127.63, 126.99, 125.00, 119.86, 73.47, 71.02, 70.70, 67.15, 56.75, 46.94; HRMS calcd for $C_{26}H_{25}O_6N_1Cs=(M+Cs)^+$ 470.1580, found 470.1562.

Synthesis of N-(δ-O-Benzyl-glutaryl)-(L)-γ-benzloxy-allo-threonyl-(2-O-acetyl-α-L-fucopyranosyl)-(L)-threonine ethyl ester (100: compound shown in FIG. 7)

2-Acetyl protected fucopeptide was prepared on solid phase starting from acetylated analog of 6 (loading 0.20 mmol/g; made in the same manner of 6 with the 2-acetylated analog of L-fucose). Apart from omitting allyl isomerization and C-terminal functionalization, the synthesis follows the general protocol for the construction of fucopeptides on solid phase. After cleavage the crude product (47.1 mg highly viscous oil) was purified by column chromatography (9 g silica gel, Hex/EtOAc-gradient 1:10 to pure EtOAc) to afford 28 mg of a colorless, highly viscous oil (0.0369 mmol, 65% based on intial loading) . ¹H NMR (500 MHz, CDCl₃) d 7.52 (d, J=9.3, 1 H), 7.35–7.27 (m, 10 H), 6.72 (d, J=7.8, 1 H), 5.94–5.86 (m, 1 H), 5.36 (dd, J=17.2, 1.3, 1 H), 5.27 (d, J=10.4, 1 H), 5.11 (s, 2 H), 5.04 (d, J=3.8, 1 H), 4.91 (dd, J=10.4, 3.8, 1 H), 4.70–4.63 (m, 3 H), 4.58 (d, J=11.9, 1 H), 4.55 (d, J=11.9, 1 H), 4.54 (dd, J=13.1, 5.9, 1 H), 4.37 (dq, J=6.3, 1.8, 1 H), 4.13–3.94 (m, 3 H), 3.77 (q, J=6.6, 1 H), 3.72 (s, br, 1 H), 3.68 (d, br, J 9.6, 1 H), 3.62 (d, br, J=9.6, 1 H), 3.37 (d, J=5.6, 1 H), 2.90 (s, br, 1 H), 2.42–2.35 (m, 2 H), 2.27–2.25 (m, 2 H), 1.96–1.90 (m, 2 H), 1.21. (d, J=6.5, 3 H), 1.11 (d, J=6.3, 3 H); ¹³C NMR (100 MHz, CDCl₃) d 172.96, 172.51, 171.23, 171.02, 170.02, 137.60, 135.76, 131.11, 128.58, 128.46, 128.32, 128.26, 127.86, 127.74, 119.44, 93.96, 76.40, 73.40, 72.48, 72.05, 71.32, 71.24, 67.79, 66.51, 66.39, 66.31, 56.88, 54.38, 35.01, 33.18, 20.87, 20.59, 16.22, 16.04; HRMS calcd for $C_{38}H_{50}Ol_4N_1Cs=(M+Cs)^+$ 891.2316, found 891.2350.

Synthesis of N-(α-O-Benzyl-succinyl)-(L)-g-benzyloxy-allo-threonyl-(2-O-acetyl-α-L-fucopyranosyl)-(L)-threonine ethyl ester (200; compound shown in FIG. 7):

2-Acetyl protected fucopeptide was prepared on solid phase starting from resin bound acetylated analog of 6 (loading 0.20 mmol/g; made in the same manner of 6 with the 2-acetylated analogy of L-fucose). Apart from omitting allyl isomerization and C-terminal functionalization, the synthesis follows the general protocol for the construction of fucopeptides on solid phase. After cleavage the crude product (52.5 mg highly viscous oil) was purified by column chromatography (6 g silica gel, Hex/EtOAc-gradient 1:8 to pure EtOAc) to afford 25 mg of a colorless, highly viscous oil (0.036 mmol, 78% based on intial loading). ¹H NMR (500 MHz, CDCl₃) d 7.50 (d, J=9.2, 1 H), 7.37–7.28 (m, 10 H), 6.86 (d, J=7.9, 1 H), 5.93–5.86 (m, 1 H), 5.35 (dd, J=17.2, 1.1, 1 H), 5.28 (d, J=10.5, 1 H), 5.10 (s, 2 H), 5.04 (d, J=3.8, 1 H), 4.90 (dd, J=10.3, 3.8, 1 H), 4.73–4.70 (m, 1 H), 4.68–4.64 (m, 2 H), 4.58 (d, J=11.8, 1 H), 4.54 (d, J=11.8, 1 H), 4.54 (t, J~13.0, 1 H), 4.37 (dq, J=6.3, 1.7, 1 H), 4.04–3.99 (m, 2 H), 3.93 (dd, J=10.4, 3.0, 1 H), 3.76 (q, J~6.6, 1 H), 3.70 (d, J=2.6, 1 H), 3.68 (dd, J=9.6, 4.4, 1 H), 3.65 (dd, J=9.6, 3.8, 1 H), 3.29 (s, br, 1 H), 2.88 (s, br, 1 H), 2.73 (dt, J=17.4, 7.1, 1 H), 2.64 (dt, J=17.4, 6.4, 1 H), 2.51 (t, J 6.8, 2 H), 2.08 (s, 3 H), 1.20 (d, J=6.6, 3 H), 1.11 (d, J=6.3, 3 H); 13C NMR (125 MHz, CDCl) d 172.59, 171.70, 171.23, 170.88, 170.03, 137.66, 136.86, 131.10, 128.55, 128.44, 128.30, 128.20, 127.82, 127.73, 119.42, 93.79, 73.37, 72.29, 72.06, 71.20, 67.80, 66.61, 66.49, 66.30, 56.91, 54.55, 30.64, 29.30, 20.85, 16.11, 16.03; HRMS calcd for $C_{37}H_{48}O_{14}N_1Cs=(M+Cs)^+$ 877.2160, found 877.2193.

Synthesis of N-(9-Fluorenylmethoxycarbonyl)-[2-O-benzyl-3,4-O-(p-acetoxymethyl)-benzylidene-α-L-fucopyranosyl]-(L)-threonine allyl ester (5) as illustrated in FIG. 4

To a solution of diol 4 (824 mg, 1.4 mmol) and dimethyl acetal 7 (467 mg, 2.6 mmol) in dry $CH_2Cl_2$ (24 ml) was added a catalytic amount of p-TsOH*$H_2O$ (14 mg, 0.07 mmol). The solution was stirred for 1 h, before sat. $NaHCO_3$ was added. The reaction mixture was diluted with EtOAc, washed with brine, dried over $MgSO_4$ and concentrated in vacuo. The crude product was purified by column chromatography (130 g silica gel, gradient Hex/$Et_2O$ 1:2 to 1:4) to afford 802 mg of a colorless foam (1.1 mmol, 78%) as a mixture of diastereomers, ratio a:b 1.1:$^1$H NMR (400 MHz, $CDCl_3$) d 7.77 (d, J=7.5, 2 H), 7.65–7.62 (m, 2 H), 7.45–7.19 (m, 13 H), 6.11 (d, J=9.4, 1 H-b), 6.06 (d, J=9.4, 1 H-a), 5.98 (s, 1 H-b), 5.97–5.88 (m, 1 H), 5.89 (s, 1 H-a), 5.40–5.23 (m, 2 H), 4.93 (d, J=3.6, 1 H-b), 4.81 (d, J=3.6, 1 H-a), 4.78–4.3.6 (m, 13 H), 4.26 (t, J=6.9, 1 H), 4.07 (d, J=5.8, 1 H), 3.97–3.90 (m, 1 H), 3.65 (dd, J=7.9, 3.7, 1 H-b), 3.53 (dd, J=7.5, 3.6, 1 H-a), 2.08 (t, J=5.9, 1 H-b), 1.98 (t, J=5.9, 1 H-a), 1.35–1.24 (m, 6 H); $^{13}$C NMR (100 MHz, $CDCl_3$) d 170.38/170.33, 156.98/156.94, 143.93/143.69, 142.07/141.93, 141.23, 138.43, 137.78, 137.65, 136.40, 131.39/131.32, 128.51, 128.39, 128.22, 128.02, 127.45, 127.83, 127.65, 127.03, 126.93, 126.83, 125.17/125.10, 119.92/119.02, 103.53/102.35, 93.77/93.38, 78.35, 76.53/76.39, 75.80, 75.06, 73.35, 72.59, 71.69/71.57, 67.18, 66.11, 64.81/64.77, 63.46, 58.86, 47.11, 16.35/16.18, 15.43/15.30; HRMS calcd for $C_{43}H_{45}O_{10}N_1Cs=(M+Cs)^+868.2098$, found 868.2131.

Synthesis of N-(9-Fluorenylmethoxycarbonyl)-[2-O-benzyl-3,4-O-(p-acetoxymethyl)-benzylidene-α-L-fucopyranosyl]-(L)-threonine allyl ester, solid phase bound (6) as illustrated in FIG. 4

Immobilization of 5: After drying 3.85 g (0.26 mmol/g, 1.0 mmol on resin) of carboxyl functionalized resin for several hours at high vacuum, 4-DMAP (12.2 mg, 0.1 mmol) and a solution of 1.545 g (2.1 mmol, 2.1 eq) of alcohol 5 in dry $CH_2Cl_2$ (16 ml) were added and the suspension was shaken gentle for 14 h at rt. The reaction mixture was transferred into a peptide synthesis vessel, filtered and after washing thoroughly with dry $CH_2Cl_2$, the resin was dried at high vacuum to give 4.32 g of material. The combined filtrates were concentrated in vacuo and excess of not reacted alcohol 5 (740 mg, 1.0 mmol, 48%) was recovered after purification by column chromatography on silica gel. Fmoc-cleavage of dry resin followed by photometric analysis revealed a loading of ~0.24 mmol/g (~1.04 mmol on resin, 100% functionalization).

Synthesis of N-(9-Fluorenylmethoxycarbonyl)-2-O-benzyl-[α-L-fucopyranosyl]-(L)-threonine (3,6,9-trioxa)-nonadecyl amide (300) as shown in FIG. 7 by Scheme shown in FIG. 5

Starting from solid phase supported fucose threonine conjugate 6, allyl isomerization, C-terminal functionalization (amide bond formation) and cleavage was conducted according to general procedures to furnish 48 mg of a colorless, amorphous solid. The crude product (contained free amine resulting from Fmoc-cleavage) was purified by column chromatography (7 g silica gel, EtOAc) to afford 22 mg of colorless, waxy solid (0.026 mmol, 66% yield based on initial loading). $^1$H NMR (400 MHz, $CDCl_3$) d 7.76 (d, J=7.5, 2 H), 7.64 (d, J=7.4, 2 H), 7.41–7.26 (m, 9 H), 7.06 (t, J~5.3, 1 H), 6.46 (d, J=7.7, 1 H), 4.95 (d, J=3.4, 1 H), 4.69 (d, J=11.7, 1 H), 4.60 (d, J=11.7, 1 H), 4.49–4.38 (m, 3 H), 4.29 (dd, J=7.6, 2.2, 1 H), 4.25 (t, J=7.0, 1 H), 3.97–3.50 (m, 13 H), 3.45 (t, J 4.6, 2 H), 3.41 (t, J=6.9, 2 H), 3.30–3.25 (m, 1 H), 2.64 ( s, br, 1 H), 2.51 (s, br, 1 H), 1.58–1.52 (m, 2 H), 1.29–1.22 (m, 17 H), 1.07 (d, J=6.2, 3 H), 0.87 (t, J 6.8, 3 H); $^{13}$C NMR (100 MHz, $CDCl_3$) d 169.85, 156.43, 143.81, 141.71, 141.26, 137.79, 128.56, 128.14, 17.69, 127.04, 125.13, 125.06, 119.95, 91.91, 76.38, 73.03, 72.20, 71.51, 70.46, 70.26, 70.04, 69.74, 69.58, 69.11, 66.99, 65.99, 59.12, 47.15, 39.47, 31.85, 29.58, 29.53, 29.43, 29.41, 29.28, 25.96, 22.64, 16.06, 14.09, 13.20; HRMS calcd for $C_{48}H_{68}O_{11}N_2Cs=(M+Cs)^+981.3877$, found 981.3913.

Synthesis of N-(d-O-Benzyl-glutaryl)-(L)-γ-benzyloxy-allo-threonyl-(2-O-benzyl-a-L-fucopyranosyl)-(L)-threonine ethyl ester (400) as illustrated in FIG. 7: scheme shown in FIG. 5

The crude cleavage product (76 mg of a colorless highly viscous oil) was purified by carefully conducted column chromatography on silica gel (10 g, gradient: Hex/EtOAc 1:8 to EtOAc) to afford a colorless solid (49 mg, 0.0616 mmol, 62% yield based on initial loading of resin).1H NMR (500 MHz, $CDCl_3$) d 8.05 (d, J=9.4, 1 H), 7.35–7.26 (m, 15 H), 6.73 (d, J=7.4, 1 H), 5.08 (s, 2 H), 4.77 (t, J 7.2, 1 H), 4.76 (d, J=3.4, 1 H), 4.67 (dd, J=9.4, 1.5, 1 H), 4.59 (d, J=12.0, 1 H), 4.58 (d, J=11.7, 1 H), 4.53 (d, J=12.0, 1 H), 4.43 (d, J=11.7, 1 H), 4.39 (dq, J=6.2, 1.5, 1 H), 4.32 (d, J=7.4, 1 H), 4.20 (dq, J=10.8, 7.2, 1 H), 4.07 (dq, J=10.8, 7.1, 1 H), 4.04–4.01 (m, 1 H), 3.97 (s, br, 1 H), 3.89 (s, br, 1 H), 3.85 (d, br, J=10.1, 1 H), 3.71 (dd, J=9.9, 3.5, 1 H), 3.69–3.60 (m, 3 H), 3.10 (s, br, 1 H), 2.40–2.30 (m, 2 H), 2.24–2.16 (m, 2 H), 1.94 (qui, J=7.4, 2 H), 1.26 (t, J=7.2, 3 H), 1.21 (d, J=6.6, 3 H), 1.06 (d, J=6.2, 3 H); $^{13}$C NMR (125 MHz, $CDCl_3$) d 172.85, 172.49, 170.89, 170.10, 137.72, 137.43, 135.79, 128.79, 128.60, 128.53, 128.34, 128.28, 128.23, 128.20, 127.81, 127.69, 92.14, 76.84, 73.49, 73.39, 71.79, 71.54, 71.10, 69.75, 68.85, 66.39, 66.25, 61.47, 56.81, 55.54, 34.99, 33.21, 20.60, 16.09, 14.39, 13.99; HRMS calcd for $C_{42}H_{54}O_{13}N_2Na=(M+Na)^+817.3524$, found 817.3560.

Synthesis of N-(δ-O-Benzyl-succinyl)-(L)-γ-benzyloxy-allo-threonyl-(2-O-benzyl-α-L-fucopyranosyl)-(L)-threonine ethyl ester (500) as shown in FIG. 7 and scheme shown in FIG. 5

The crude cleavage product (75 mg of a highly viscous oil) was purified by carefully conducted column chromatography on silica gel (6 g, Hex/EtOAc 1:10) to afford a colorless solid (51 mg, 0.0651 mmol, 65% yield based on initial loading of resin). $^1$H NMR (500 MHz, $CDCl_3$) d 8.06 (d, J=9.4, 1 H), 7.37–7.27 (m, 15 H), 6.63 (d, J=7.6, 1 H), 5.10 (s, 2 H), 4.79 (t, br, J 7.2, 1 H), 4.77 (d, J=3.1, 1 H), 4.68 (d, J=9.4, 1 H), 4.59 (d, J=12.0, 1 H), 4.58 (d, J=11.7, 1 H), 4.53 (d, J=12.0, 1 H), 4.41 (d, J=11.7, 1 H), 4.40–4.37 (m, 1 H), 4.31 (d, J=7.2, 1 H), 4.21–4.17 (m, 1 H), 4.10–4.03 (m, 2 H), 3.98 (s, br, 1 H), 3.91 (s, br, 1 H), 3.84 (d, br, J=9.9, 1 H), 3.71 (dd, J=10.1, 2.5, 1 H), 3.67–3.63 (m, 3 H), 3.14 (s, br, 1 H), 2.75–2.62 (m, 2 H), 2.49–2.44 (m, 2 H), 1.26 (dt, J=7.2, 1.5, 3 H), 1.21 (d, J=6.5, 3 H), 1.06 (d, J=6.1, 3 H); $^{13}$C NMR (125 MHz, $CDCl_3$) d 172.52, 171.67, 170.83, 170.11, 137.39, 137.41, 135.65, 128.81, 128.61, 128.51, 128.33, 128.29, 128.23, 128.15, 127.81, 127.67, 92.10, 76.79, 73.46, 73.38, 71.80, 71.52, 71.11, 69.73, 68.85, 66.48, 66.40, 61.48, 56.80, 55.63, 30.59, 29.30, 16.09, 14.38, 13.99; HRMS calcd for $C_{41}H_{52}O_{13}N_2Cs=(M+Cs)^+$ 913.2524, found 913.2566.

Synthesis of N-(δ-O-Benzyl-glutaryl)-(L)-g-benzyloxy-allo-threonyl-(2-O-benzyl-α-L-fucopyranosyl)-(L)-threonine (3,6,9-trioxa)-nonadecyl ester (600) as shown in FIG. 7 and scheme shown in FIG. 5

The crude cleavage product (108 mg of a highly viscous oil) was purified by carefully conducted column chromatography on silica gel (12 g, gradient: Hex/EtOAc 1:8 to EtOAc) to afford a slightly yellow, highly viscous oil (49 mg, 0.0471 mmol, 47% yield based on initial loading of resin). $^1$H NMR (500 MHz, CDCl$_3$) d 8.13 (d, J=9.5, 1 H), 7.37–7.25 (m, 15 H), 6.66 (d, J=7.6, 1 H), 5.10 (s, 2 H), 4.77 (d, J=3.5, 1 H), 4.75 (dd, J=7.4, 6.4, 1 H), 4.72 (dd, J=9.5, 1.5, 1 H), 4.60 (d, J=11.8, 1 H), 4.56 (d, J=11.9, 1 H), 4.52 (d, J=11.9, 1 H), 4.45 (d, J=11.8, 1 H), 4.40 (dq, J=6.2, 1.5, 1 H), 4.35–4.28 (m, 2 H), 4.14–4.05 (m, 2 H), 4.03–3.98 (m, 1 H), 3.88–3.84 (m, 2 H), 3.71–3.52 (m, 14 H), 3.42 (t, J=6.9, 2 H), 3.08 (s, br, 1 H), 2.42–2.32 (m, 2 H), 2.27–2.17 (m, 2 H), 1.94 (qui, J=7.4, 2 H), 1.56 (qui, J=6.9, 2 H), 1.31–1.25 (m, 14 H), 1.21 (d, J=6.6, 3 H), 1.07 (d, J=6.2, 3 H), 0.88 (t, J~6.9, 3 H); $^{13}$C NMR (125 MHz, CDCl$_3$) d 172.85, 172.40, 170.83, 170.24, 137.74, 137.61, 135.79, 128.55, 128.34, 128.19, 127.80, 127.69, 92.43, 76,62, 73.39, 73.23, 71.72, 71.67, 71.49, 71.39, 70.54, 70.46, 70.40, 70.11, 69.87, 68.78, 68.61, 66.25, 65.18, 64.66, 56.92, 55.27, 41.88, 35.00, 33.22, 31.84, 30.05, 29.55, 29.51, 29.43, 29.27, 25.99, 22.62, 20.58, 16.07, 14.63, 14.07; HRMS calcd for $C_{56}H_{82}O_{16}N_2Cs=(M+Cs)^+$ 1171.4719 found 1171.4770.

Synthesis of N-(d-O-Benzyl-glutaryl)-(L)-y-benzyloxy-allo-threonyl-(2-O-benzyl-α-L-fucopyranosyl)-(L)-threonine (3,6.9-trioxa)-nonadecyl amide (700) as shown in FIG. 7 and scheme shown in FIG. 5

The crude cleavage product (106 mg of a colorless highly viscous oil) was purified by carefully conducted column chromatography on silica gel (12 g, gradient: EtOAc to EtOAc/EtOll 10:1) to afford a colorless, highly viscous oil (60 mg, 0.0578 mmol, 58% yield based on initial loading of resin). $^1$H NMR (500 MHz, CDCl$_3$) d 8.05 (d, J=9.0, 1 H), 7.89 (t, J 4.0, 1 H), 7.36–7.24 (m, 15 H), 6.59 (d, J=7.7, 1 H), 5.12 (s, 2 H), 4.85 (d, J=3.6, 1 H), 4.73 (d, J=7.7, 1 H), 4.63–4.54 (m, 3 H), 4.55 (d, J=11.7, 1 H), 4.48 (d, J=11.8, 1 H), 4.45 (dd, J=9.0, 1.4, 1 H), 3.86–3.80 (m, 3 H), 3.68 (dd, J=9.8, 3.5, 1 H), 3.63–3.40 (m, 16 H), 3.37 (t, J=7.0, 2 H), 3.25–3.20 (m, 1 H), 2.51 (s, br, 1 H), 2.40 (dt, J=7.4, 3.1, 2 H), 2.28–2.19 (m, 2 H), 1.96 (qui, J=7.4, 2 H), 1.57–1.21 (m, 2 H), 1.30–1.23 (m, 14 H), 1.23 (d, J=6.7, 3 H), 1.10 (d, J=6.3, 3 H), 0.88 (t, J~6.9, 3 H); $^{13}$C NMR (125 MHz, CDCl$_3$) d 172.39, 171.55, 170.67, 169.34, 139.04, 138.20, 136.13, 128.33, 128.07, 128.01, 127.85, 127.79, 127.60, 127.45, 127.28, 127.10, 93.14, 75.58, 72.20, 71.86, 71.42, 71.15, 70.22, 70.15, 69.68, 69.57, 69.50, 69.35, 68.59, 68.34, 65.27, 57.13, 54.41, 38.62, 33.90, 32.69, 31.20, 29.10, 28.95, 28.88, 28.78, 28.61, 25.55, 22.01, 20.51, 16.29, 15.02, 13.87; HRMS calcd for $C_{57}H_{83}O_{15}N_3Cs=(M+Cs)$+1170.4879, found 1170.4961.

Figure 8:
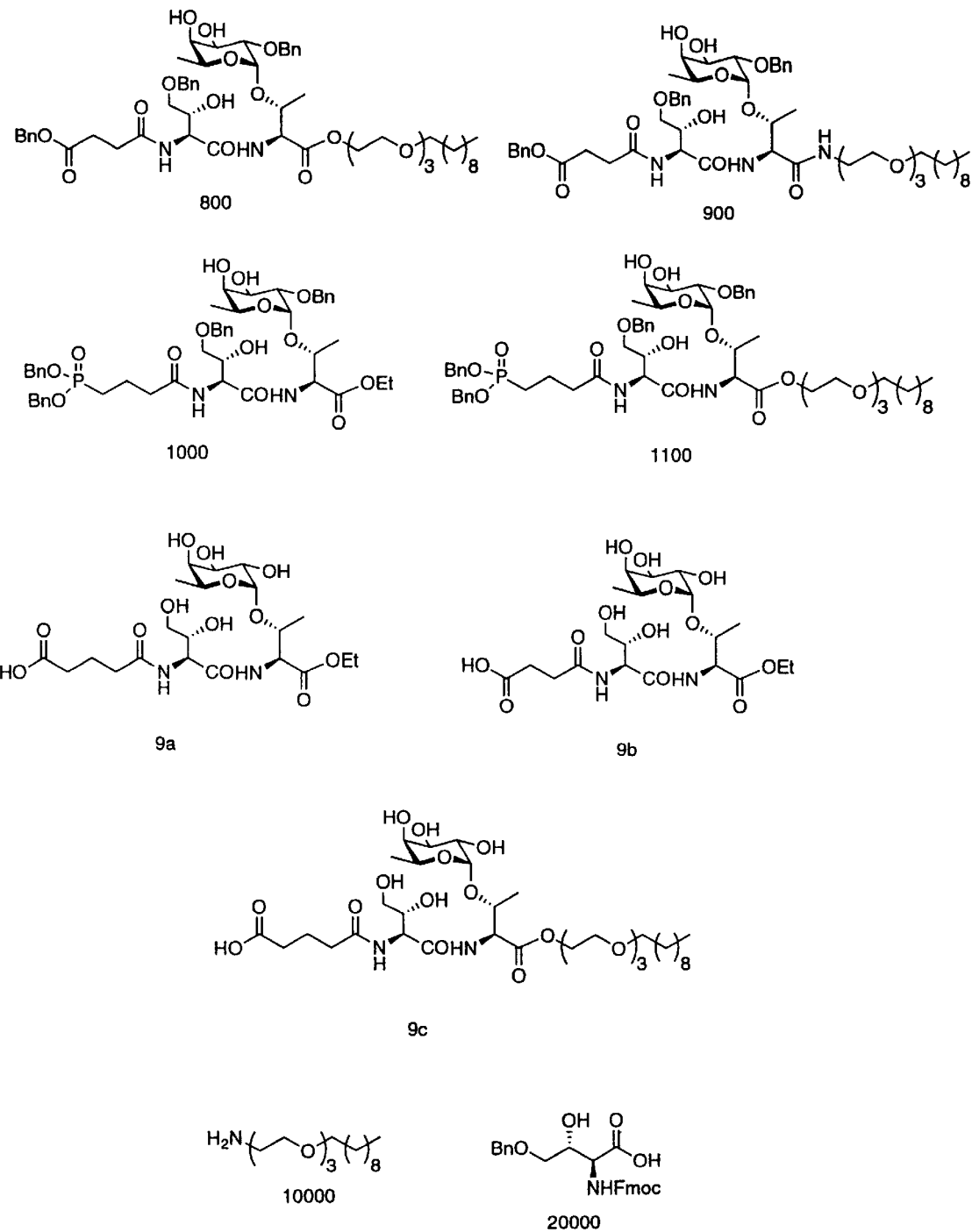
FIG. 8 shows new mimetics (800–1400) and reagents 10000, and 20000; some of the mimetics have activity against P-selectin with $IC_{50}$ values in the low mM range.

Synthesis of N-(d-O-Benzyl-succinyl)-(L)-benzyloxy-allo-threonyl-(2-O-benzyl-α-L-fucopyranosyl)-(L)-threonine (3,6,9-trioxa)-nonadecyl ester (800) as shown in FIG. 8 and scheme shown in FIG. 5

The crude cleavage product (104 mg of a colorless highly viscous oil) was purified by twofold column chromatography on silica gel (12 g, gradient: Hex/EtOAc 1:8 to 1:10 to EtOAc) to afford a colorless highly viscous oil (50 mg, 0.049 mmol, 62% yield based on initial loading of resin). $^1$H NMR (500 MHz, CDCl$_3$) d 8.12 (d, J=9.4, 1 H), 7.36–7.25 (m, 15 H), 6.79 (d, J=7.7, 1 H), 5.09 (s, 2 H), 4.79 (d, J=3.3, 1 H), 4.75 (t, J~6.8, 1 H), 4.72 (d, J=9.3, 1 H), 4.60 (d, J=11.8, 1 H), 4.54 (s, br, 2 H), 4.49 (d, J=11.8, 1 H),4.40 (q, br, J 6.1, 1 H), 4.33–4.28 (m, 1 H), 4.10–4.02 (m, 2 H), 3.87–3.83 (m, 2 H), 3.71–3.52 (m, 15 H), 3.42 (t, J=6.8, 2 H), 2.76–2.61 (m, 2 H), 2.50–2.45 (m, 2 H), 1.58–1.32 (m, 2 H), 1.32–1.23 1(m, 14 H), 1.21 (d, J=6.4, 3 H), 1.08 (d, J=6.2, 3 H), 0.86 (t, J 6.8, 3 H); $^{13}$C NMR (125 MHz, CDCl$_3$) d 172.54, 171.57, 170.71, 170.33, 137.84, 137.63, 135.95, 128.57, 128.53, 128.34, 128.23, 128.16, 127.81, 127.69, 92.47, 76.52, 73.39, 73.19, 71.73, 71.50, 70.52, 70.43, 70.40, 70.17, 69.86, 68.79, 68.63, 66.48, 66.20, 64.70, 56.97, 55.33, 31.85, 30.64, 29.57, 29.53, 29.49, 29.45, 29.33, 29.28, 26.00, 22.64, 16.07, 14.70, 14.09; HRMS calcd for $C_{55}H_{80}O_{16}N_2Cs=(M+Cs)^+$1157.4562 found 1157.4508.

Synthesis of N-(d-O-Benzylsuccinyl)-(L)-γ-benzyloxy-allo-threonyl-(2-O-benzyl-α-L-fucopyranosyl)-(L)-threonine (3,6,9-trioxa)-nonadecyl amide (900) as shown in FIG. 8 and scheme shown in FIG. 5

The crude cleavage product (97 mg of a slightly yellow, highly viscous oil) was purified by twofold column chromatography on silica gel (8 g, EtOAc) to afford a colorless, highly viscous oil (52 mg, 0.0508 mmol, 51% yield based on initial loading of resin). $^1$H NMR (500 MHz, CDCl$_3$) d 7.88 (d, J=9.0, 1 H), 7.89 (s, br, 1 H), 7.36–7.24 (m, 15 H), 6.71 (d, J=7.6, 1 H), 5.11 (s, 2 H), 4.86 (d, J=3.4, 1 H), 4.72 (t, J=7.5, 1 H), 4.60 (d, J=11.9, 1 H), 4.59 (d, J=11.8, 1 H), 4.53 (d, J=11.8, 1 H), 4.51 (d, J=7.2, 1 H), 4.47 (d, J=11.9, 1 H), 4.46 (d, J=8.9, 1 H), 3.86–3.81 (m, 3 H), 3.69–3.40 (m, 16 H), 3.37 (t, J=6.9, 2 H), 3.29–3.25 (m, 1 H), 2.76 (dt, J=17.2, 7.2, 1 H), 2.65 (dt, J=17.2, 6.4, 1 H), 2.56 (s, br, 1 H), 2.51 (t, J=6.8, 2 H), 2.41 (s, br, 1 H), 1.54 (qui, J=6.6, 2 H), 1.32–1.23 (m, 14 H), 1.23 (d, J=7.0, 3 H), 1.09 (d, J=6.2, 3 H), 0.88 (t, J&19 6.9, 3 H); $^{13}$C NMR (125 MHz, CDCl$_3$) d 172.49, 172.22, 170.24, 169.87, 137.71, 135.63, 128.60, 128.52, 128.39, 128.32, 128.22, 128.13, 127.82, 91.76, 76.50, 73.36, 73.01, 72.57, 72.12, 71.84, 71.42, 70.42, 70.11, 69.81, 69.68, 69.56, 68.96, 68.38, 66.46, 65.78, 58.52, 54.65, 39.64, 31.85, 30.65, 29.58, 29.54, 29.44, 29.41, 29.28, 29.24, 25.98, 22.64, 16.02, 14.48, 14.09; HRMS calcd for $C_{55}H_{81}O_{15}N_3CS=(M+Cs)^+$1156.4722, found 1156.4775.

Synthesis of N-(4-(Dibenzyl-phosphonate)-butanoyl)-(L)γ-benzyloxy-allo-threonyl-(2-O-benzyl-α-L-fucopyranosyl)-(L)-threonine ethyl ester (1000) as shown in FIG. 8 and scheme shown in FIG. 5

The crude cleavage product (109 mg of a colorless highly viscous oil) was purified by carefully conducted column chromatography on silica gel (8 g, gradient: EtOAc/EtOH 50:1 to 30:1) to afford a colorless oil/foam (62 mg, 0.0673 mmol, 67% yield based on initial loading of resin). $^1$H NMR (500 MHz, CDCl$_3$) d 7.78 (d, J=9.6, 1 H), 7.32–7.21 (m, 20 H), 6.75 (d, J=7.4, 1 H), 5.03–4.90 (m, 4 H), 4.81 (d, J=2.9, 1 H), 4.72 (t, br, J~6.2, 1 H), 4.67 (d, J=9.7, 1 H), 4.62–4.52 (m, 3 H), 4.45 (d, J=11.6, 1 H), 4.38 (q, br, J 6.2, 1 H), 4.24–4.14 (m, 2 H), 4.09–4.01 (m, 2H), 3.89–3.83 (m, 2 H), 3.75–3.62 (m, 4 H), 3.05 (s, br, 1 H), 2.18–2.09 (m, 2 H), 1.92–1.69 (m, 4 H), 1.25 (t, br, J~6.9, 3 H), 1.22 (d, J=6.5, 3 H), 1.09 (d, J=6.1, 3 H); $^{13}$C NMR (125 MHz, CDCl) d 172.28, 170.04, 137.73, 137.68, 136.15, 128.67, 128.54, 128.54, 128.36, 128.17, 127.87, 127.75, 127.68, 92.42, 73.40, 73.34, 71.69, 71.15, 70.05, 68.78, 67.28, 67.23, 66.30 61.45, 56.73, 55.41, 35.70 (d, J$^2$=14), 24.70 (d, J$^1$=137), 18.35 (d, J$^3$=4), 1612, 1462, 13.98; HRMS calcd for $C_{48}H_{61}O_{14}N_2P_1Cs=(M+Cs)^+$1053.2915, found 1053.2962.

Synthesis of N(4-(Dibenzyl-phosphonate)-butanoyl)-(L)-γ-benzyloxy-allo-threonyl-(2-O-benzyl-α-L-fucopyranosyl)-(L)-threonine (3,6,9-trioxa)-nonadecyl ester (1100) as shown in FIG. 8 and scheme shown in FIG. 5

The crude cleavage product (113 mg of a highly viscous oil) was purified by carefully conducted column chromatography on silica gel (10 g, gradient: EtOAc/EtOH 35:1 to 25:1) to afford a colorless, highly viscous oil (64 mg, 0.0549 mmol, 55% yield based on initial loading of resin). $^1$H NMR (500 MHz, CDCl$_3$) d 7.91 (s, br, 1 H), 7.36–7.25 (m, 20 H), 6.86 (s, br, 1 H), 5.04–4.91 (m, 4 H), 4.84 (d, J=3.4, 1 H), 4.71–4.68 (m, 2 H), 4.63 (d, J=11.7, 1 H), 4.56–4.52 (m, 3 H), 4.40 (dq, J=6.3, 1.5, 1 H), 4.32–4.27 (m, 1 H), 4.23–4.11 (m, 4 H), 3.89 (d, br, J=9.4, 1 H), 3.74 (s, br, 1 H), 3.70–3.52 (m, 14 H), 3.41 (t, J=6.9, 2 H), 2.78 (s, br, 1 H), 2.18 (t, br, J 6.6, 2 H), 1.97–1.73 (m, 4 H), 1. 57–1.52 (m, 2 H), 1. 30–1.23 (m, 14 H), 1.21 (d, J=6.6, 3 H), 1.12 (d, J=6.2, 3 H), 0.88 (t, J~6.9, 3 H); $^{13}$C NMR (125 MHz, CDCl$_3$) d 171.20, 171.01, 170.15, 137.74, 137.70, 136.12, 128.52, 128.47, 128.35, 128.31, 128.06, 127.85, 127.81, 127.78, 127.74, 127.64, 92.61, 76.50, 73.34, 73.21, 71.77, 71.45, 71.23, 71.19, 70.46, 70.41, 70.34, 20.27, 69.81, 68.72, 68.57, 67.19, 67.18 (d, J$^2$=12.9), 66.21, 64.56, 56.79, 55.22, 35.64 (d, J2=13.9), 31.80, 29.52, 29.48, 29.46, 29.39, 29.23, 25.96, 24.60 (d, J$^1$=140.9), 22.59, 18.29 (d, J$^3$=3.9), 16.06, 14.69, 14.04; HRMS calcd for $C_{62}H_{89}O_{17}N_2P_1Cs=(M+Cs)^+$ 1297.4953 found 1297.5008.

Synthesis of N(Glutaryl)-(L)-γ-hydroxy-allo-threonyl-α-L-fucopyranosyl-(L)-threonine ethyl ester (9a) as shown in FIG. 8 and scheme shown in FIG. 5

According to the general hydrogenation protocol benzylated fucopeptide 800 (39 mg, 0.049 mmol) was deprotected to yield 22.6 mg of a colorless, fluffy solid (0.043 mmol, 88%) after work up. $^1$H NMR (500 MHz, D$_2$O) d 4.96 (d, J=3.8, 1 H), 4.69 (d, J=1.9, 1 H), 4.53 (d, J=7.2, 1 H), 4.42 (dq, J=6.3, 1.9, 1 H), 4.22 (dq, J=10.7, 7.2, 1 H), 4.12 (dq, J=10.7, 7.2, 1 H), 3.97 (dt, J=6.8, 3.3, 1 H), 3.75–3.67 (m, 5 H), 3.60 (dd, J=12.2, 6.3, 1 H), 2.36–2.31 (m, 4 H), 1.84 (qui, J=7.4, 2 H), 1.24 (t, J=7.2, 3 H), 1.16 (d, J=5.9, 3 H), 1.15 (d, J=6.2, 3 H); $^{13}$C NMR (125.MHz, D$_2$O) d 176.79, 172.98, 172.65, 95.41, 72.54, 71.81, 70.39, 68.59, 67.94, 67.94, 63.94, 63.30, 58.21, 56.11, 35.37, 34.19, 21.66, 16.20, 15.08, 14.26; HRMS calcd for $C_{21}H_{36}O_{13}N_2Cs=(M+Cs)^+$657.1272, found 657.1294.

Synthesis of N-(Succinyl)-(L)-hydroxy-allo-threonyl-α-L-fucopyranosyl-(L)-threonine ethyl ester (9b) as shown in FIG. 8 and scheme shown in FIG. 5

According to the general hydrogenation protocol benzylated fucopeptide 800 (45 mg, 0.058 mmol) was deprotected to yield 28.8 mg of a colorless solid (0.056 mmol, 97%) after work up. $^1$H NMR (500 MHz, D$_2$O) d 8.73 (d, J 8.8, 0.3 H), 4.95 (d, J=3.5, 1 H), 4.68 (s, br, 1 H), 4.54 (d, J=7.2, 1 H), 4.44 (q, br, J~6.1, 1 H), 4.22 (dq, J=10.6, 7.2, 1 H), 4.12 (dq, J=10.6, 7.2, 1 H), 3.97 (m, 1 H), 3.74–3.69 (n, 5 H), 3.60 (dd, J=12.1, 6.4, 1 H), 2.62–2.52 (m, 4 H), 1.24 (t, J=7.1, 3 H), 1.15 (d, br, J 6.4, 6 H); $^{13}$CNR (125 MHz, D$_2$O) d 177.89, 175.62, 172.96, 172.65, 95.39, 72.54, 71.91, 71.77, 70.37, 68.61, 67.94, 63.94, 63.28, 58.21, 56.02, 30.95, 30.10, 16.20, 15.06, 14.26; HRMS calcd for $C_{20}H_{34}IO_{13}N_2Cs=(M+Cs)^+$643.1115, found 643.1139.

N-(Glutaryl)-(L)-hydroxy-allo-threonyl-a-L-fucopyranosyl)-(L)-threonine (3,6,9-trioxa)-nonadecyl ester (9c) as shown in FIG. 8 and scheme shown in FIG. 5

According to the general hydrogenation protocol benzylated fucopeptide 600 (44 mg, 0.042 mmol) was deprotected to yield 25.4 mg of a colorless, fluffy solid (0.032 mmol, 76%) after work up. $^1$H NMR (500 MHz, D$_2$O) d 4.93 (d, J=3.8, 1 H) , 4.70 (s, br, 1 H), 4.57 (d, J=7.2, 1 H), 4.42–4.34 (m, 2 H), 4.18–4.14 (n, 1 H), 3.98–3.95 (m, 1 H), 3.75–3.60 (m, 14 H), 3.54 (s, br, 2 H), 3.42 (t, J=6.6, 2 H), 2.34–2.31 (m, 4 H), 1.84 (qui, J=7.4, 2 H), 1.53 (s, br, 2 H), 1.29–1.22 (m, 14 H), 1.17 (d, J=6.0, 3 H), 1.15 (d, J=6.3, 3 H), 0.85 (t, J~6.6, 3 H); $^{13}$C NMR (125 MHz, D$_2$O) d 179.04, 176.34, 172.71, 95.58, 72.61, 72.02, 91.95, 71.70, 70.96, 70.86, 70.81, 70.62, 70.52, 69.33, 68.70, 67.76, 65.98, 63.37, 58.04, 56.00, 35.50, 34.40, 32.85, 30.64, 30.58, 30.44, 30.30, 30.28, 26.91, 23.54, 21.80, 16.59, 15.35, 14.81; HRMS calcd for $C_{35}H_{64}O_{16}N_2Cs=(M+Cs)^+$901.3310, found 901.3343.

Figure 9:
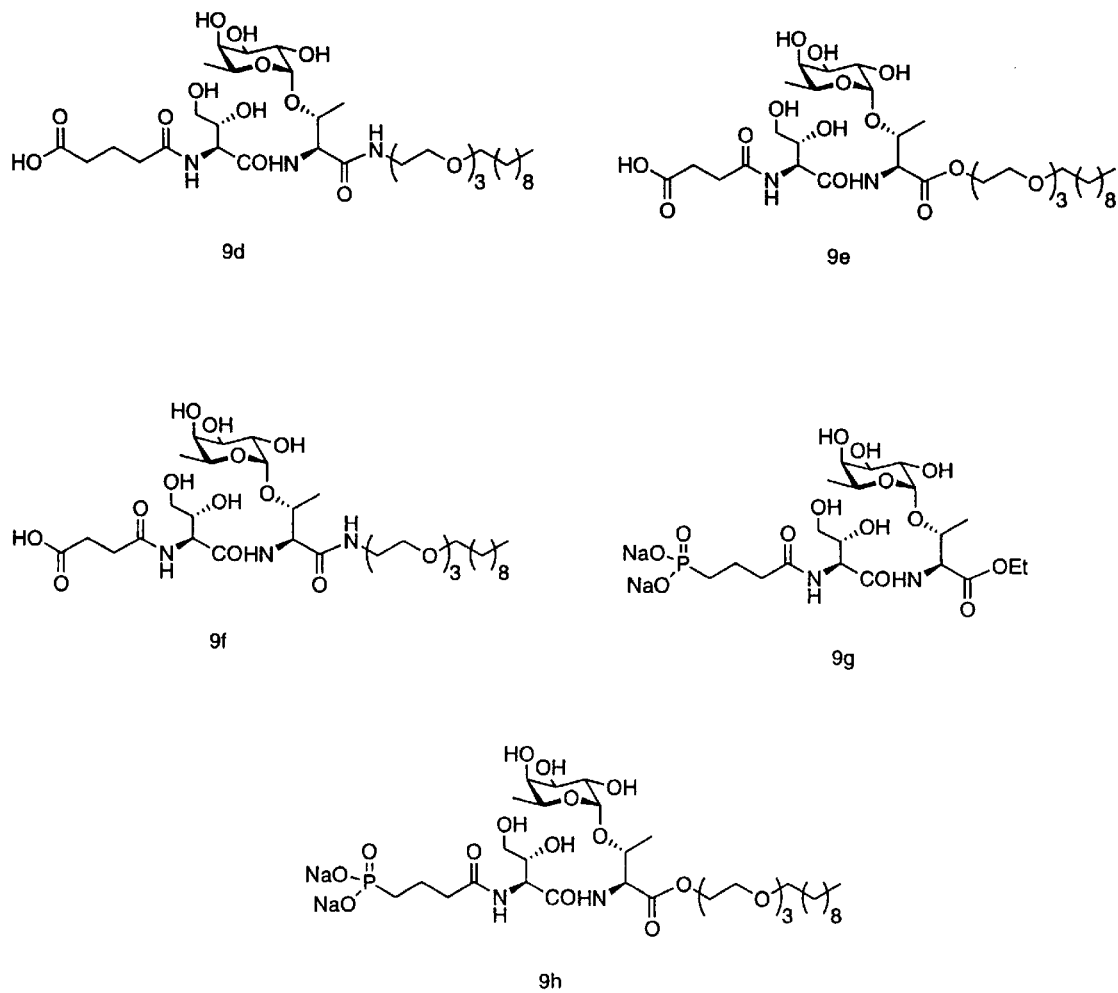
FIG. 9 illustrate new mimetics (1500–1900), some of which have activity against P-selectin with $IC_{50}$ values in the low mM range.

N-(Glutaryl)-(L)-hydroxy-allo-threonyl-α-L-fucopyranosyl)-(L)-threonine (3,6,9-trioxa)-nonadecyl amide (9d) as shown in FIG. 9 and scheme shown in FIG. 5

According to the general hydrogenation protocol benzylated fucopeptide 700 (56 mg, ~90% pure, 0.054 mmol) was deprotected to yield 27.9 mg of a colorless, fluffy solid (0.036 mmnol, 67%) after work up. $^1$H NMR (500 MHz, D$_2$O) d 4.94 (d, J=3.7, 1 H), 4.53 (d, J=9.0, 1 H), 4.44 (s, br, 1 H), 4.41 (d, J=6.3, 1 H), 3.89–3.87 (m, 1 H), 3.75–3.52 (m, 16 H), 3.43 (t, J=6.7, 2 H), 3.31–3.36 (m, 2 H), 2.34–2.31 (m, 4 H), 2.29 (t, J~7.1, 2 H), 2.24 (t, J=7.4, 2 H), 1.81 (qui, J~7.3, 2 H), 1.28–1.21 (m, 14 H), 1.18 (d, J=6.1, 3 H), 1.14 (d, J=6.4, 3 H), 0.83 (t, J~6.6, 3 H); $^{13}$C NMR (125 MHz, D$_2$O) d 176.84, 173.91, 172.43, 95.17, 72.75, 72.07, 70.79, 70.69, 70.62, 70.49, 69.75, 68.77, 67.71, 63.45, 59.27, 55.51, 40.17, 35.82, 35.66, 32.80, 30.57, 30.51, 30.34, 30.25, 30.14, 26.82, 23.51, 22.39, 16.49, 15.19, 14.80; HRMS calcd for $C_{35}H_{65}O_{15}N_3Cs=(M+Cs)^+$900.3470, found 900.3498.

N-(Succinyl)-(L)-hydroxy-allo-threonyl-a-L-fucopyranosyl)-(L)-threonine (3,6,9-trioxa)-nonadecyl ester (9e) as shown in FIG. 9 and scheme shown in FIG. 5

According to the general hydrogenation protocol benzylated fucopeptide 800 (45 mg, 0.044 mmol) was deprotected to yield 26.9 mg of a colorless, fluffy solid (0.036 mmol, 81%) after work up. $^1$H NMR (500 MHz, D$_2$O) d 4.94 (d, J=3.8, 1 H), 4.70 (s, br, 1 H), 4.58 (d, J=7.2, 1 H), 4.42–4.35 (m, 2 H), 4.18–4.16 (m, 1 H), 3.97–3.96 (m, 1 H), 3.74–3.55 (m, 15 H), 3.42 (t, J=6.5, 1 H), 2.64–2.55 (m, 4 H), 1.53 (s, br, 2 H), 1.30–1.23 (m, 14 H), 1.17 (d, J=6.1, 3 H), 1.15 (d, J=6.5, 3 H), 0.85 (t, J~6.5, 3 H); $^{13}$C NMR (125 MHz, D$_2$O) d 177.60, 175.22, 172.71, 172.02, 95.57, 72.61, 72.08, 72.01, 71.66, 70.96, 70.88, 70.82, 70.64, 70.51, 69.33, 68.71, 67.75, 65.97, 63.34, 32.91, 31.05, 30.68, 30.61, 30.48, 30.33, 30.14, 26.95, 23.56, 16.59, 15.35, 14.81; HRMS calcd for $C_{34}H_{62}O_{16}N_2Cs=(M+Cs)^+887.3154$, found 887.3184.

N-(Succinyl)-(L)-hydroxy-allo-threonyl-α-L-fucopyranosyl)-(L)-threonine (3,6,9-trioxa)-nonadecyl amide (9f)

as shown in FIG. 9 and scheme shown in FIG. 5

According to the general hydrogenation protocol benzylated fucopeptide 500 (52 mg, 0.051 mmol) was deprotected to yield 36.5 mg of a colorless, fluffy solid (0.048 mmol, 95%) after work up. $^1$H NMR (500 MHz, D$_2$O) d 4.92 (d, J=3.6, 1 H), 4.54 (d, J=8.7, 1 H), 4.43 (s, br, 1 H), 4.40 (d, J=6.3, 1 H), 3.88–3.86 (m, 1 H), 3.75–3.51 (m, 16 H), 3.41 (t, J=6.6, 1 H), 3.38–3.29 (m, 2 H), 2.61–2.52 (m, 4 H), 1.52 (s, br, 2 H), 1.29–1.21 (m, 14 H), 1.16 (d, J=6.0, 3 H), 1.13 (d, J=6.4, 3 H), 0.82 (t, J~6.6, 3 H); $^{13}$C NMR (125 MHz, D$_2$O) d 177.85, 175.63, 173.80, 172.54/172.46, 95.23, 72.81, 72.58, 72.13, 70.88, 70.75, 70.67, 70.60, 69.81, 68.83, 67.76, 63.48, 59.37, 55.62, 40.34/40.32, 32.91, 31.09, 30.73, 30.65, 30.50, 30.39, 30.28, 26.97, 23.61, 16.55, 15.27, 14.87; HRMS calcd for $C_{34}H_{63}O_{15}N_3Cs=(M+Cs)^+$ 886.3314, found 886.3344.

N-(4-Phosphonate-butanoyl)-(L)-hydroxy-allo-threonyl-a-L-fucopyranosyl)-(L)-threonine ethyl ester disodium salt (9g) as shown in FIG. 9 and scheme shown in FIG. 5

According to the general hydrogenation protocol phosphonate 1000 (60 mg, 0.065 mmol) was deprotected to yield 37 mg of a colorless, fluffy solid (0.061 mmol, 94%) after work up and ion exchange to sodium. $^1$H NMR (500 MHz, D$_2$O) d 4.95 (d, J=3.6, 1 H), 4.68 (s, br, 1 H), 4.52 (d, J=7.2, 1 H), 4.52 (d, J=7.2, 1 H), 4.43–4.38 (m, 1 H), 4.25–4.18 (m, 1 H), 4.15–4.08 (m, 1 H), 3.98–3.94 (m, 1 H), 3.75–3.66 (m, 5 H), 3.61 (dd, J=12.1, 6.4, 1 H), 2.37–2.32 (m, 4 H), 1.81–1.73 (m, 2 H), 1.56–1.47 (m, 2 H), 1.24 (d, J=7.1, 3 H), 1.15 (d, J 6.6, 3 H); $^{13}$C NMR (125 MHz, D$_2$O) d 177.13, 172.98, 172.66, 95.35, 72.51, 71.77, 70.81, 68.54, 67.89, 63.91, 63.25, 58.19, 56.03, 37.25 (d, $J^{2-17}$), 28.22 (d, $J^1$=133), 20.92 (d, $J^3$=3.3), 16.18, 15.06, 14.25; HRMS calcd for $C_{20}H_{35}O_{14}N2Na_2CS=(M+Cs)^+605.1699$, found 605.1719.

N-(4-Phosphonate-butanoyl)-(L)-hydroxy-allo-threonyl-α-L-fucopyranosyl)-(L)-threonine (3,6,9-trioxa)-nonadecyl amide disodium salt (9h) as shown in FIG. 9 and scheme shown in FIG. 5

According to the general hydrogenation protocol phosphonate 1100 (61 mg, 0.052 mmol) was deprotected to yield 40.3 mg of a colorless, fluffy solid (0.047 mmol, 91%) after work up and ion exchange to sodium. $^1$H NMR (500 MHz, D$_2$O) d 4.94 (d, J=3.5, 1 H), 4.72 (s, br, 1 H), 4.56 (d, J=7.2, 1 H), 4.42–4.34 (m, 2 H), 4.19–4.15 (m, 1 H), 3.97–3.94 (m, 1 H), 3.7–3.55 (m, 16 H), 3.44 (t, J=6.7, 2 H), 2.39–2.29 (m, 2 H), 1.81–174 (m, 2 H), 1.56–1.47 (m, 4 H), 1.28–1.23 (m, 14 H), 1.17 (d, J=6.0, 3 H), 1.15 (d, J=6.5, 3 H), 0.85 (t, J~6.6, 3 H); $^{13}$C NMR (125 MHz, D$_2$O) d 177.04, 172.84, 172.06, 95.48, 72.63, 72.01, 71.89, 71.74, 70.94, 70.81, 70.80, 70.56, 70.45, 69.31, 68.65, 67.76, 65.94, 63.32, 58.02, 55.97, 37.41 (d, $J^2$=17.4), 32.81, 30.57, 30.51, 30.33, 30.26, 30.16, 28.40 (d, $J^1$=132.8), 26.83, 23.53, 21.05, 16.58, 16.26, 14.84; HRMS calcd for $C_{34}H_{63}O_{17}N_2Na_2Cs$ (M+Cs)$^+$849.3738, found 849.3702.

While a preferred form of the invention has been shown in the drawings and described, since variations in the preferred form will be apparent to those skilled in the art, the invention should not be construed as limited to the specific form shown and described, but instead is as set forth in the following claims.

What is claimed is:

1. A sialyl Lewis mimetic represented by the following structure:

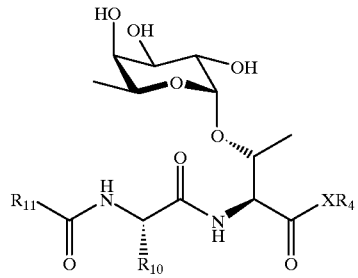

wherein:

X is a radical selected from a group consisting of —O— and —NH—;

$R_4$ is hydrogen or a radical selected from a group consisting of —(CH$_2$CH$_2$—O—)$_n$—(CH$_2$)$_m$—CH$_3$ —(C$_1$–C$_{20}$ alkyl), -phenyl, -benzyl, -nitrobenzyl, -trityl, -allyl, -furoyl, -cinnamoyl, -thiophenesulfonyl, [—CH$_n$CO$_2$—(C$_1$–C$_{20}$ alkyl) —CH$_n$CO$_2$-allyl, and —Ch$_n$CO$_2$H] —(CH$_2$)$_n$CO$_2$—(C$_1$–C$_{20}$ alkyl), —(CH$_2$)$_n$ CO$_2$-allyl, and —(CH$_2$)$_n$CO$_2$H;

$R_{10}$ is a radical selected from a group consisting of —CH(OH)—CH$_2$(OH), —CH(OBn)—CH$_2$—(OH), and CH(OH)—CH$_2$—(OBn);

$R_{11}$ is a radical selected from a group consisting of —(CH$_2$)$_p$CO$_2$H, —(CH$_2$)$_p$CO$_2$Bn, —(CH$_2$)$_p$PO(OBn)$_2$, and —(CH$_2$)$_p$PO(OH)$_2$;

$1 \leq n \leq 10$;

$1 \leq m \leq 10$; and $1 \leq p \leq 5$;

with the following proviso:
if $R_1$ is hydrogen or —(C$_1$–C$_{20}$ alkyl), then $R_{11}$ is neither —(CH$_2$)$_3$CO$_2$H nor —(CH$_2$)$_3$CO$_2$Bn.

2. A library of Sialyl Lewis mimetics comprising a plurality of compounds according to claim 1.

3. A method for generating a Sialyl Lewis mimetic according to claim 1 comprising the following steps:

Step A: attaching an intermediate represented by the following structure:

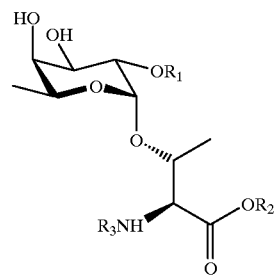

wherein $R_1$ is an alcohol blocking group; $R_2$ is a carboxy acid blocking group; and $R_3$ is an amine blocking group;

to an anchor molecule represented by the following structure:

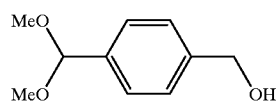

for forming a benzylidene acetal having a free hydroxyl moiety represented by the following structure:

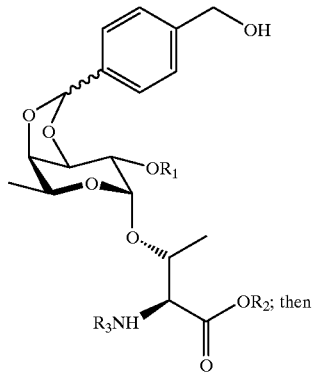

Step B: anchoring the free hydroxyl moiety of the benzylidene acetal as described in said step A to a support molecule having a terminal carboxylic acid group for forming a first immobilized fucoside represented by the following structure:

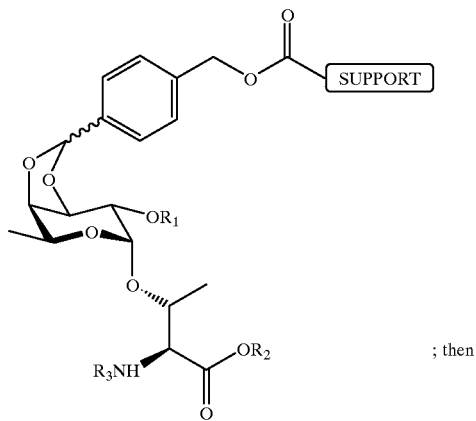

Step C: deblocking said carboxy acid blocking group ($R_2$) of the first immobilized fucoside as described in said Step B for forming a second immobilized fucoside having a free C-terminal carboxy acid group; then Step D: reacting the free C-terminal carboxy acid group as described in said Step C with a nucleophile represented by the formula: $R_4$-XH wherein X is a radical selected from a group consisting —O— and —NH—; $R_4$ is a radical selected from a group consisting of —$(CH_2CH_2-O-)_n$—$(CH_2)_m$—$CH_3$, —($C_1$–$C_{20}$ alkyl), -phenyl, -benzyl, -nitrobenzyl, -trityl, -allyl, -furoyl, -cinnamoyl, -thiophenesulfonyl, —$(CH_2)_nCO_2$—($C_1$–$C_{20}$ alkyl), —$(CH_2)_nCO_2$-allyl and —$(CH_2)_nCO_2H$ $1 \leq n \leq 10$; $1 \leq m \leq 10$;

for forming a first C-terminal functionalized immobilized fucoside represented by the formula:

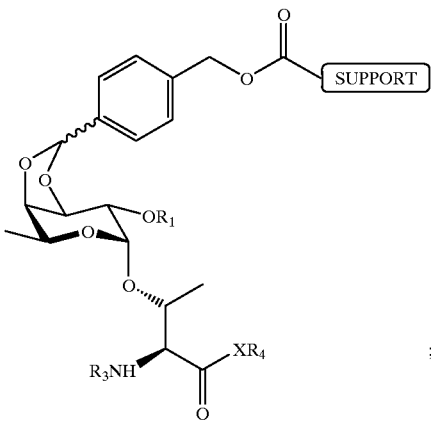

Step E: deblocking said amino blocking group ($R_3$) of the first C-terminal functionalized immobilized fucoside as described in said Step D for forming a second C-terminal functionalized immobilized fucoside having a first free N-terminal amino group, then Step F: reacting the first free N-terminal amino group as described in said Step E with an acceptor represented by the formula: $R_{12}NH(CHR_6)_nCOY$ wherein $R_6$ is a radical selected from a group consisting of —$CH(OR_7)$—$CH_2$ ($OR_8$); $R_7$ and $R_8$ are independently selected from a group consisting of hydrogen, phenyl and benzyl;

Y is a radical selected from a group consisting of hydrogen and chloride; $R_{12}$ is an amine blocking group; for forming a first C/N-terminal functionalized immobilized fucoside; then Step G: deblocking said amino blocking group ($R_{12}$) of the first C/N-terminal functionalized immobilized fucoside as described in said Step F for forming a second C/N-terminal functionalized immobilized fucoside having a second free N-terminal amino group; then Step H: reacting the second free N-terminal amino group as described in said Step G with an acceptor represented by the formula: $R_9COY$ wherein $R_9$ is a radical selected from a group consisting of —$(CH_2)_pCO_2Bn$, and —$(CH_2)_pPO(OBn)_2$; Y is a radical selected from a group consisting of hydrogen and chloride; $1 \leq p \leq 5$; for forming a fully functionalized immobilized fucoside represented by the following structure:

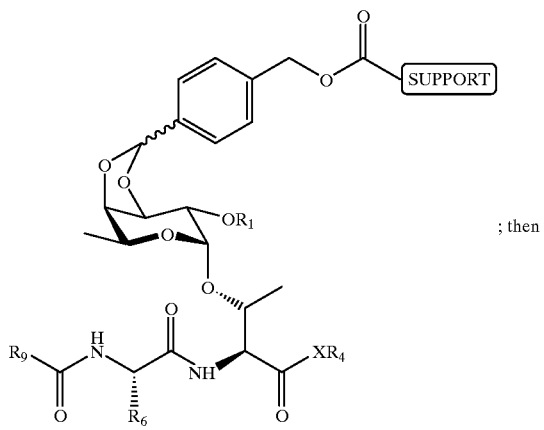

Step I: cleaving the fully functionalized immobilized fucoside as described in said step H from the support molecule for forming an advanced intermediate represented by the following structure:

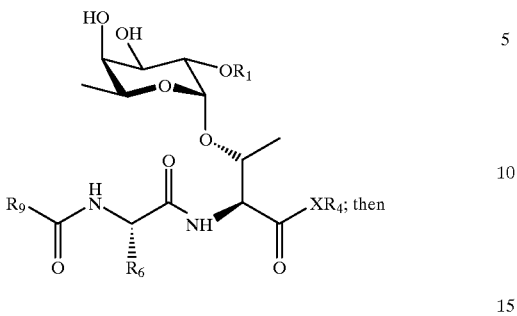

Step J: deprotecting the $R_1$ group, the $R_6$ group and the $R_9$ group of the advanced intermediate as described in said step I for forming sSialyl Lewis mimetics represented by the following structure:

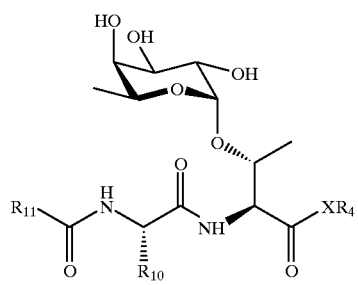

wherein $R_{10}$ is a radical represented by the formula: —CH(OH)—CH$_2$(OH); $R_{11}$ is a radical selected from a group consisting of —(CH$_2$)$_p$CO$_2$H, and —(CH$_2$)$_p$PO(OH)$_2$.

* * * * *